United States Patent
Hong et al.

(10) Patent No.: US 11,931,472 B1
(45) Date of Patent: Mar. 19, 2024

(54) VEHICLE WITH UVC LIGHT EMITTERS

(71) Applicant: Zoox, Inc., Foster City, CA (US)

(72) Inventors: Chang Gi Samuel Hong, San Francisco, CA (US); James Michael Eccleston, Foster City, CA (US); Andrew Frank Raczkowski, San Jose, CA (US); Goutham Shanmuga Sundaram, Foster City, CA (US); Andrew Mark Stieber, Foster City, CA (US)

(73) Assignee: Zoox, Inc., Foster City, CA (US)

( * ) Notice: Subject to any disclaimer, the term of this patent is extended or adjusted under 35 U.S.C. 154(b) by 365 days.

(21) Appl. No.: 17/127,073

(22) Filed: Dec. 18, 2020

(51) Int. Cl.
  *A61L 2/10* (2006.01)
  *A61L 2/26* (2006.01)
  *B60H 1/00* (2006.01)
  *B60R 25/24* (2013.01)

(52) U.S. Cl.
  CPC .................. *A61L 2/10* (2013.01); *A61L 2/26* (2013.01); *A61L 2202/11* (2013.01); *A61L 2202/14* (2013.01); *A61L 2202/25* (2013.01); *B60H 2001/0015* (2013.01); *B60Q 2500/20* (2013.01); *B60R 25/24* (2013.01)

(58) Field of Classification Search
  CPC .......... A61L 2/10; A61L 2/26; A61L 2202/11; A61L 2202/14; A61L 2202/25; B60H 2001/0015; B60Q 2500/20; B60R 25/24
  See application file for complete search history.

(56) References Cited

U.S. PATENT DOCUMENTS

| | | | |
|---|---|---|---|
| 11,007,292 B1* | 5/2021 | Grenon | A61L 2/24 |
| 2007/0053188 A1* | 3/2007 | New | B60Q 3/43 |
| | | | 362/276 |
| 2014/0232268 A1 | 8/2014 | Kamoi | |
| 2015/0273092 A1 | 10/2015 | Holub | |
| 2017/0100989 A1* | 4/2017 | Chapaton | B60H 3/0085 |
| 2018/0370322 A1* | 12/2018 | Filipkowski | B60H 1/0055 |
| 2019/0076558 A1 | 3/2019 | Zhang-Miske | |

(Continued)

FOREIGN PATENT DOCUMENTS

| | | |
|---|---|---|
| JP | 2018181260 | 11/2018 |
| KR | 100998473 | 12/2010 |

(Continued)

OTHER PUBLICATIONS

Cameron, "Introducing the Voyage G3 Robotaxi", Voyage, Aug. 26, 2020, 14 pgs.

(Continued)

*Primary Examiner* — David E Smith
(74) *Attorney, Agent, or Firm* — Lee & Hayes, P.C.

(57) ABSTRACT

A system for disinfecting an autonomous vehicle includes a light assembly having LEDs configured to emit UVC light into a passenger compartment of the autonomous vehicle. The light assembly includes a heat sink to dissipate heat generated by the LEDs. In examples, the heat sink is disposed in the path of forced air associated with a climate control system of the vehicle. The climate control system may be controlled based on a temperature proximate the LEDs and/or the heat sink. In some examples, the light assembly is integrated into the ceiling of the vehicle and can further include visible light emitters and/or other features.

20 Claims, 9 Drawing Sheets

(56) References Cited

U.S. PATENT DOCUMENTS

| | | | |
|---|---|---|---|
| 2019/0091738 A1 | 3/2019 | Chen | |
| 2020/0009286 A1 | 1/2020 | Zarcone | |
| 2020/0167722 A1 | 5/2020 | Goldberg | |
| 2021/0187140 A1 | 6/2021 | Spazier | |
| 2021/0393823 A1* | 12/2021 | Childress | B64D 13/00 |
| 2021/0394590 A1 | 12/2021 | Kyle | |
| 2021/0402041 A1 | 12/2021 | Whinnery | |
| 2022/0088249 A1 | 3/2022 | Kyle | |
| 2022/0088250 A1 | 3/2022 | Baarman | |
| 2022/0111089 A1* | 4/2022 | Childress | B64D 47/02 |
| 2022/0125975 A1 | 4/2022 | MacKenzie | |
| 2022/0184249 A1* | 6/2022 | Childress | A61L 2/10 |
| 2022/0184250 A1* | 6/2022 | Childress | A61L 2/10 |
| 2022/0268458 A1* | 8/2022 | Torresan | B60H 1/00371 |

FOREIGN PATENT DOCUMENTS

| | | |
|---|---|---|
| KR | 20200036114 | 4/2020 |
| WO | WO2019014023 | 1/2019 |
| WO | WO2019070733 | 4/2019 |

OTHER PUBLICATIONS

Office Action for U.S. Appl. No. 17/127,163, dated Dec. 14, 2022, Hong, "Method of Disinfecting Vehicle Using UVC Light Emitters", 25 Pages.

* cited by examiner

VEHICLE WITH UVC LIGHT EMITTERS

BACKGROUND

Many vehicles are used for ridesharing. For example, taxi services have historically been staples in major cities. More recently, autonomous vehicles are being contemplated for ridesharing. For instance, autonomous vehicles may be a robotic alternative to conventional, manned techniques for moving people and cargo. While autonomous vehicles may be suited to perform the primary task of a driver, e.g., moving a passenger or cargo, many autonomous vehicles are unconventionally able to perform other tasks generally performed by a driver or other human. For instance, it may be important to disinfect, sanitize, or otherwise clean features within a passenger compartment of an autonomous vehicle.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical components or features.

DETAILED DESCRIPTION

Figure 1:
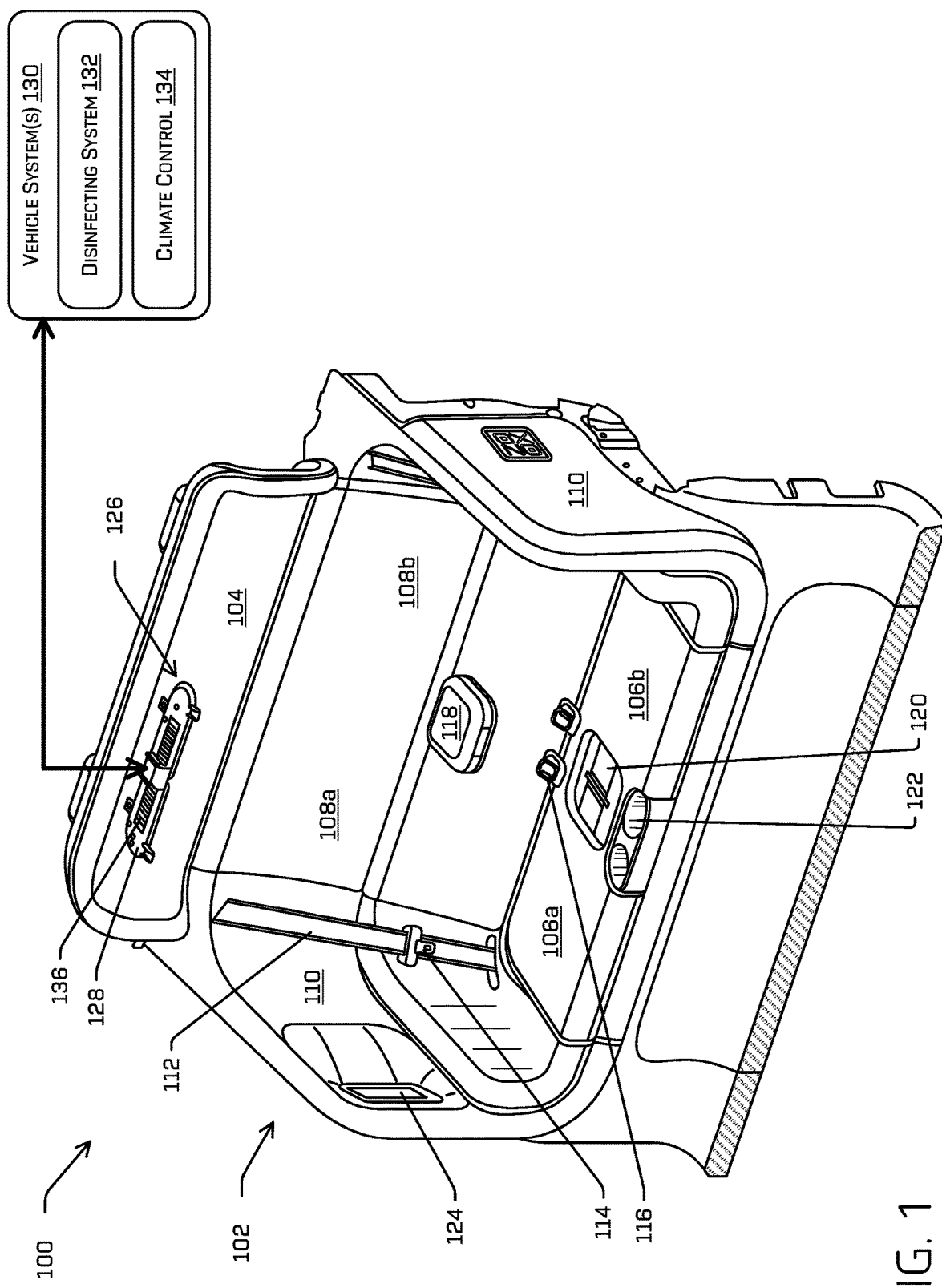
FIG. 1 illustrates a perspective view of aspects of an example vehicle seating arrangement including a light assembly with a disinfecting system, as described herein.

Disclosed herein are techniques directed to disinfecting vehicles. In some examples, the techniques more particularly relates to lighting assemblies with integrated ultraviolet (UV) light emitters that can disinfect surfaces in a vehicle. In certain examples, the techniques pertain to methods of controlling an autonomous vehicle and vehicle subsystems to disinfect surfaces in the vehicle.

As briefly described above, shared spaces are prone to becoming dirty, and vehicles used for ridesharing are not an exception. Vehicles include numerous features, including but not limited to seats, headrests, seat belts, buttons, switches, knobs, ports, caddies, cupholders, and the like, for passengers to touch, manipulate, and/or control. With each contact, pathogens, such as viruses, bacteria, and germs, may be left for the next passenger(s) who interact with those features. Conventionally, cleanliness in a ridesharing vehicle has been left to the driver. However, autonomous vehicles do not have the benefit of a driver to clean and disinfect the passenger compartment after every ride. Additionally, human instigated disinfection may be unreliable in thoroughness and/or consistency.

The following techniques are directed to systems and techniques for disinfecting a passenger compartment in an autonomous fashion. For instance, the systems and techniques described herein may be particularly well suited to a level-5 autonomous vehicle, but the systems and techniques can be used in other vehicles as well.

In some examples, disinfecting systems described herein can include a lighting assembly with integrated UV (or Ultraviolet C (UVC)) light-emitting LEDs. In examples of this disclosure, surfaces within a passenger compartment of a vehicle are exposed to UVC light emitted by LEDs at an intensity and/or duration sufficient to eliminate pathogens on those surfaces. In at least some examples, a plurality of LEDs are provided to ensure adequate exposure to quickly and effectively eliminate pathogens. In some examples, the lighting assembly may be disposed above or proximate a passenger seating area, to expose those surfaces most likely contacted by passengers.

In some instances, the lighting assembly incorporating the UVC light-emitting LEDs may also incorporate various additional functionalities and features. For instance, in addition to including the UVC light-emitting LEDs, the lighting assembly can include one or more visible light emitters and/or one or more user interface features. The light emitters may be used to illuminate portions of the interior of the vehicle, e.g., for passenger convenience. In other examples, the light emitters may be configurable to emit visible light of different wave lengths, e.g., to indicate a status of the vehicle. For example, the visible light emitters can emit red, purple, or some other light, or may emit light according to a predetermined pattern, e.g., flashing or strobing, to indicate that a vehicle is undergoing UVC light disinfection.

In some examples, the lighting assembly can also incorporate aspects of a climate control system. For instance, lighting assemblies according to this disclosure can integrate a vent opening in fluid communication with a heating, ventilation, and air conditioning (HVAC) or similar system that supplies temperature-regulated air to the passenger compartment. Conventionally, such systems are used for passenger comfort. Aspects of this disclosure may use the climate control system to dissipate heat generated by LEDs emitting UVC light to achieve, for example, dense packaging of UVC-emitting LEDs. To achieve quick and effective cleaning using UVC-light, examples described herein may use a plurality of LEDs, including LEDs closely situated. UVC light-emitting LEDs are known to generate relatively large thermal loads as compared to other LEDs, which, especially in number, could cause damage to components of the vehicle (such as the UVC LEDs themselves) if unregulated. However, according to some aspects of this disclosure, the lighting assembly may include a heat sink to dissipate heat generated by the LEDs, and the heat sink may be disposed in a path of temperature-regulated air supplied to a passenger compartment via one or more vent openings integrated into the lighting assembly. Accordingly, lighting assemblies such as those described herein may provide active cooling for the LEDs, e.g., by passing refrigerated air over the heat sink. In some examples a fluid (such as a refrigerant liquid) can be used to regulate thermal emissions of an LED assembly. The fluid can be coupled to an air conditioning or other cooling system of a vehicle (e.g., a radiator, engine, or other cooling system).

In some example methods, a vehicle may be disinfected by activating UVC light-emitting LEDs to expose surfaces of the vehicle to the UVC light. However, UVC light can be harmful to passengers and/or other types of cargo. Accordingly, example techniques described herein can include determining that a passenger compartment is empty prior to activating the UVC-emitting LEDs. For instance, some techniques can include receiving sensor data from one or more sensors associated with the passenger compartment and determining from the sensor data that no passengers are present in the vehicle. Such sensor data can include image data, pressure data, presence data, and/or other types of data that may be used to ensure no passengers are present during a disinfection routine.

Once the vehicle is determined to be empty, the techniques described herein can ensure that the passenger compartment remains empty. For instance, techniques described herein can including configuring the vehicle in a manner to prohibit passenger ingress during the disinfection cycle. For example, doors of the vehicle may be locked and/or emitters may be configured to indicate to would-be-passengers outside the vehicle is undergoing disinfection.

In still further example techniques described herein, a disinfection routine that includes emitting UVC light may be implemented while a vehicle is travelling to a location, e.g., a location to retrieve a next passenger. In some examples, techniques described herein can determine whether a transit time to a next location, with the vehicle empty, exceeds a disinfection time for performing a disinfection routine. For instance, data from a planning system can include a transit time, and when the transit time exceeds the disinfecting time associated with a disinfecting routine, the routine may be performed during transit. Similarly, in some implementations, the planning system may be configured to select a next destination based on the transit time, e.g., to ensure that sufficient time is available to complete a disinfection routine. In examples, after a predetermined number of rides (or passengers) the planning system may prioritize performing a disinfection routine, and therefore "create" opportunities to implement the routine by selecting a next passenger that will allow sufficient time for disinfecting.

The techniques and systems described herein may be implemented in a number of ways. Example implementations are provided below with reference to the figures.

FIG. 1 illustrates a portion 100 of an interior of a vehicle, such as an automobile. In examples described herein, the vehicle may be an autonomous vehicle, although aspects of this disclosure may apply to any vehicle that includes a passenger compartment and/or certain subsystems, as detailed further herein. The portion 100 generally includes a seating area 102 and a headrest 104 associated with the seating area 102. In more detail, the seating area 102 includes a first seat portion 106a having a corresponding first seatback portion 108a and a second seat portion 106b having a corresponding second seatback portion 108b. Herein, the first seat portion 106a and the second seat portion 106b may be referred to, collectively, as the seat portions 106, and the first seatback portion 108a and the second seatback portion 108b may be referred to, collectively, as the seatback portions 108. In the example of FIG. 1, the seating area 102 may terminate at lateral sides 110, although the lateral sides 110 are shown for example only. In some instances, the lateral sides 110 may be interior, lateral sides of a vehicle in which the seating area 102 and the headrest 104 are disposed. Although the portion 100 is illustrated as including two instances of the seat portions 106 and the seatback portions 108, the seating area 102 may otherwise be configured for more or fewer passengers.

The portion 100 of the interior of the vehicle includes a number of additional components with which a passenger can interact, e.g., for safety, convenience, comfort, and/or the like. For instance, as shown in FIG. 1, the portion 100 of the interior of the vehicle can include a seat belt 112 associated with each of the seat portions 106a, 106b. The seat belt 112 is illustrated as a conventional three-point safety belt including a tongue 114 selectively receivable in a buckle 116. Although the seat belt 112 is illustrated as a three-point safety belt other types of seat belts, including but not limited to lap belts, four-point safety-belts, or the like may alternatively be included. The type and arrangement of the seat belt 112 are for example only.

The portion 100 of the interior of the vehicle also is illustrated as including an armrest 118, a charging station 120, and an accessory tray 122. In the illustrated example, the armrest 118 extends between the first seatback portion 108a and the second seatback portion 108b, e.g. to provide a surface on which a passenger in either of the seat portions 106 may rest her arm. The armrest 118 is illustrated as extending from the seatback, although in other examples the armrest 118 may be supported proximate the seat portions 106, e.g., between the buckles 116 associated with the two seat portions 106. Other examples of the armrest 118 also are contemplated. For example, and without limitation, armrests may be provided proximate the lateral sides 110 of the portion 100 of the vehicle. Such armrests may be in addition to or as an alternative to the armrest 118 centrally located in the example of FIG. 1.

The charging station 120 also is provided between the first seat portion 106a and the second seat portion 106b in the example of FIG. 1. In some instances, the charging station 120 may include one or more surfaces on which an electronic device belonging to a passenger, such as a mobile phone, tablet, or the like, may be placed, e.g., to inductively charge the device. In other examples, the charging station 120 may include one or more receptacles, connectors, cables, and/or the like to facilitate charging of one or more electronic devices associated with passengers seated in the seating portions 106a, 106b. As will be appreciated, the charging station 120 may be supplied power from a power source on the vehicle of which the portion 100 is a part. Although a single instance of the charging station 120 is illustrated in FIG. 1, e.g., as accessible to a passenger in either of the seating portions 106, multiple instances of the charging station 120 may alternatively be provided, e.g., proximate the lateral sides 110.

The accessory tray 122 is also accessible from each of the first seat portion 106a and the second seat portion 106b, e.g. such that a passenger in either of those seat portions may use the accessory tray 122. In the illustrated example, the accessory tray 122 may be configured to receive a cup or the like. However, the accessory tray 122 illustrated is for example only; other configurations and functionality for the accessory tray 122 will be appreciated. Moreover, although the accessory tray 122 is illustrated as being between the first seating portion 106a and the second seating portion 106b, in other examples multiple accessory trays 122 may be provided, e.g., proximate the sidewalls 110. For instance, the vehicle can include one accessory tray 122 accessible from the first seating portion 106a and a second instance of the accessory tray 122 accessible from the second seating portion 106b.

FIG. 1 also illustrates a user interface 124. In the illustrated example, the user interface 124 comprises a display screen disposed in the one of the lateral sides 110 proximate the first seating portion 106a. In example implementations, the user interface 124 may be a touch screen providing an interactive interface for a passenger seated in the first seating portion 106a. For example, via the user interface 124, a passenger may control aspects of the vehicle, including but not limited to seat preferences, ambient features, such as lighting, sound, or the like. Also in examples, the passenger may interact with the user interface 124 to identify a destination of travel or the like, to track progress of a trip, or otherwise provide information to (or receive information from) the vehicle. Although only a single instance of the user interface 124 is illustrated in FIG. 1, another instance of the user interface 124 may be provided in the one of the lateral sides 110 proximate the second seating portion 116b, but maybe obscured in FIG. 1. In examples, at least one instance of the user interface 124 may be provided for each seating portion in the vehicle.

In examples, the portion 100 of the vehicle may also include a lighting assembly 126. In examples, the lighting assembly 126 may be disposed in a ceiling (omitted from FIG. 1 for clarity) of the vehicle. For example, and as detailed further in this description, the lighting assembly 126 may include a housing 128 housing one or more visible light emitters (not shown in FIG. 1) associated with each of the seating portions 106. In some examples, the lighting assembly 126 may provide conventional "reading light" functionality. The lighting assembly may also be configured to selectively provide illumination for a passenger in the vehicle, e.g., to aid a passenger in entering and/or exiting the vehicle, in selecting an available seat, or the like. As also detailed further herein, the lighting assembly 126 may also include features that facilitate interactive functionality to alert the autonomous vehicle to take some action. For instance, and without limitation, the lighting assembly 126 may include a button, such as an emergency button (not shown in FIG. 1), configured to generate a signal to bring the autonomous vehicle to a stop.

As will be appreciated, the seat belt 112, the armrest 118, the charging station 120, the accessory tray 122, the user interface 124, and/or aspects of the lighting assembly 126 may be passenger accessories intended for safety and comfort of the passenger. Each of these accessories may also include interactive features and/or otherwise be intended to be manipulated, interacted with, and/or touched by passengers using the vehicle. Moreover, the portion 100 is intended to be in an enclosed space, e.g., within the autonomous vehicle and the vehicle may be intended to be used by a number of passengers, e.g., as a taxi or similar delivery system. Accordingly, germs, bacteria, viruses, and the like may be readily transferred to surfaces in the vehicle, and such pathogens may be transmitted to a next passenger using the vehicle and interacting with these features and surfaces. To limit transmission of bacteria, viruses, and the like, it may be desirable to disinfect the portion 100 of the vehicle, including the various surfaces to be interacted with by passengers, on a regular basis. However, it may be impractical to regularly remove the autonomous vehicle from service so a person can clean the interior of the vehicle.

Accordingly, aspects of this disclosure include incorporating a system and techniques for disinfecting and/or cleaning the autonomous vehicle using UVC light emitters. Such system and techniques can operate without taking the vehicle out of service, e.g., by operating between rider transport.

In some instances, and as detailed further herein, the lighting assembly 126 may include a plurality of UVC light emitters, which may be embodied as LEDs (not shown in FIG. 1). These emitters may be configured to emit UVC light on to surfaces and features of the portion 100, as detailed further herein. For instance, the emitters may be configured to emit UVC light according to one or more disinfecting routines. Without limitation, a disinfection routine can include a disinfecting time, e.g., corresponding to a duration for which UVC light emitters are activated, a disinfecting intensity, e.g., corresponding to a number of UVC light emitters that are activated and/or portions of the vehicle with which the activated UVC light emitters are associated, and a desired outcome, e.g., 99.9% clean, 40% clean, or the like. Moreover, the light assembly 126, including the UVC light emitters, may be controlled by and/or in communication with one or more vehicle systems 130. Examples of the vehicle system(s) 130 shown in FIG. 1 include a disinfecting system 132 and a climate control system 134.

In examples described further herein, the disinfecting system 132 can include functionality to control the UVC light emitters contained in the lighting assembly 126 to selectively emit UVC-light. UVC light is effective at killing bacteria, viruses, and other pathogens and incorporating the UVC light emitters in the lighting assembly 126 may well-position the emitters to emit UVC light onto the surfaces and components most often touched by passengers, and therefore more likely to carry pathogens. In some instances, the disinfecting system 132 can store details about the disinfecting routines mentioned above, including instructions for activating selected UVC light emitters at selected times, for selective durations, and/or based on different criteria. As also detailed further herein, the disinfecting system 132 may also receive information from other sources, such as sensors, planning systems, or the like. In at least some examples, the disinfecting system 132 can receive sensor data to determine whether passengers are in the vehicle, e.g., to perform a disinfecting routine only when passengers are not present. The disinfecting system 132 can also receive planning data associated with transit times, including transit times during which the vehicle is empty. The disinfecting system 132 may instruct a disinfecting routine when a transit time exceeds a time to complete a disinfecting routine, for example.

In examples of this disclosure, UVC light for disinfecting a passenger compartment may be emitted by a plurality of LEDs integrated into the lighting assembly 126. For instance, a first plurality of LEDs may be configured generally above, and directed toward, the first seating portion 106a and a second plurality of LEDs may be configured generally above, and directed to, the second seating portion 106b. The LED emitters may be located in the lighting assembly 126 to provide global coverage of surfaces within the portion 100. However, aspects of this disclosure also locate the LED emitters in the lighting assembly 126 to provide additional benefits. For example, and as detailed further below, the LED emitters may generate large thermal loads when emitting UVC-light. When multiple LEDs are used, the thermal load may be so great as to be destructive to surrounding components, including but not limited to a substrate or mount to which the LEDs are coupled and/or the LEDs themselves.

Aspects of this disclosure can improve dissipation of the of the thermal load generated by the LEDs using the climate control system 134. In some examples, the climate control system 134 may be an HVAC system e.g., configured to force temperature-regulated air into the portion 100 of the vehicle. Conventionally, the climate control system 134 may be used for passenger comfort, e.g. to regulate temperature in the autonomous vehicle for the passenger. In aspects of the present disclosure, however, the climate control system 134 may further be used to reduce a thermal load on aspects of the lighting assembly 126, as described further herein. In FIG. 1, the lighting assembly 126 is illustrated as including a plurality of openings 136. These openings may be in fluid communication with a conduit, duct, or the like that supplies forced air from a source (not shown) such that the temperature-regulated air passes into and through the lighting assembly 126 and into the passenger compartment generally shown by the portion 100. By passing cooled air through the lighting assembly 126, e.g., near the LEDs, aspects of this disclosure may provide for active cooling of the UVC light-emitting system. As a result of the active cooling, more LEDs and/or LEDs of higher power can be used in the vehicle (and/or LEDs can be operated for longer in a high-power state), thereby increasing disinfection efficacy and/or shortening disinfecting times.

Figure 2:
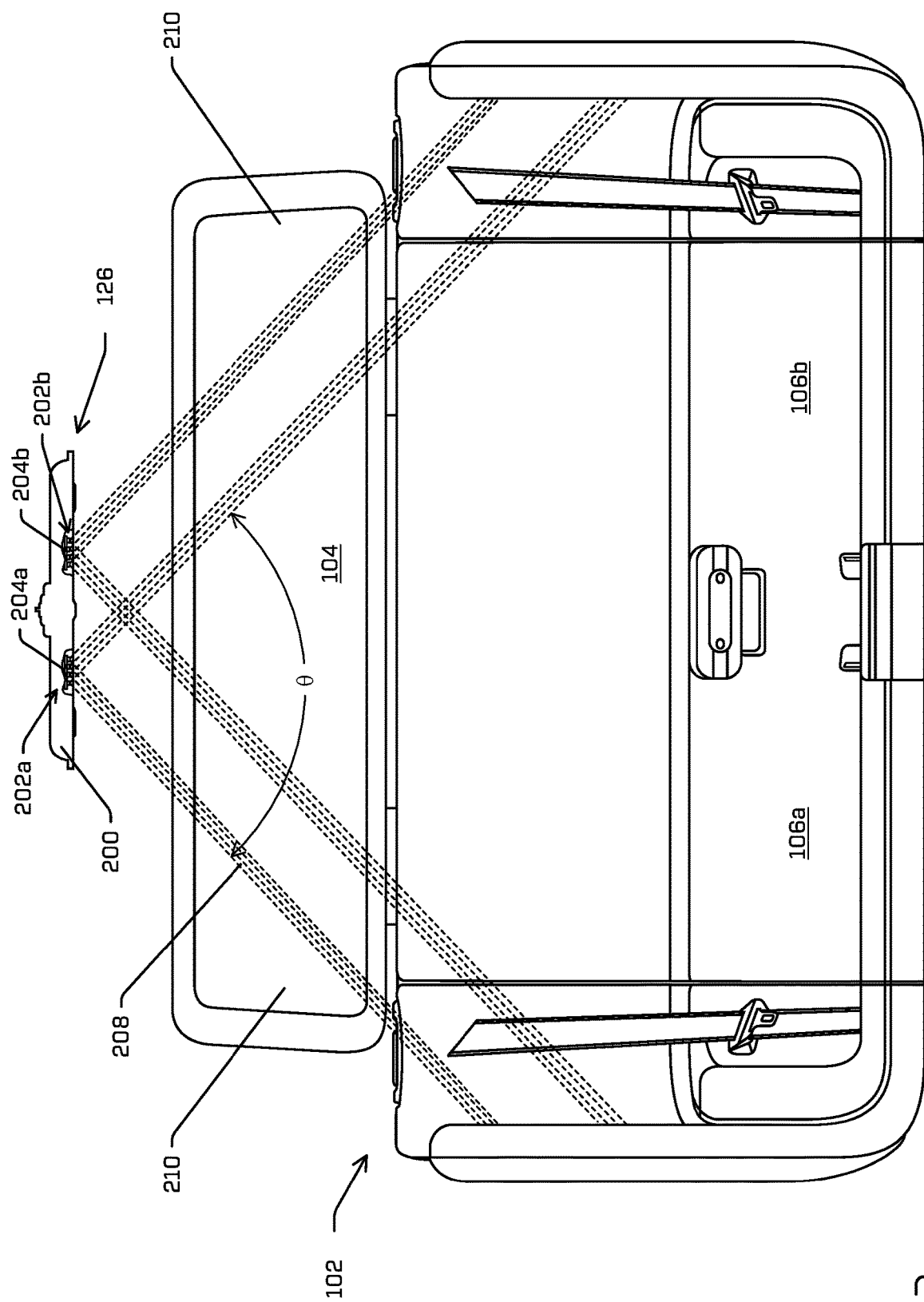
FIG. 2 is a front view of the example system of FIG. 1 schematically illustrating disinfecting using the light assembly, as described herein.

FIG. 2 is a front elevation of aspects of the portion 100 of the vehicle shown in FIG. 1. FIG. 2 shows the lighting assembly 126 disposed above the seating area 102 and schematically illustrates aspects of UVC light emission associated with the lighting assembly. As in FIG. 1, the ceiling and additional parts of a body of the vehicle are removed for clarity. In addition, a portion of a housing 200 of the lighting assembly 126 is removed, to show a plurality of first LEDs 202a and a plurality of second LEDs 202b. The first LEDs 202a are disposed on a first substrate 204a and the second LEDs 202b are disposed on a second substrate 204b. As generally illustrated in FIG. 2, the first LEDs 202a are disposed above the first seating portion 106a of the seating area 102 and the second LEDs 202b are disposed above the second seating portion 106b of the seating area 102.

In the illustrated example, the first LEDs 202a are arranged in a first array on the first substrate 204a and the second LEDs 202b are arranged in a second array on the second substrate 204b. In the illustrated example, the first array and the second array are 1×4 arrays, each consisting generally of a single line of four LEDs. As also illustrated in FIG. 2, each of the LEDs is configured to emit UVC light 208 within an emission angle, θ. The emission angle is labeled only for one of the LEDs in the first LEDs 202a, but, as generally illustrated in FIG. 2, each of the LEDs may have a similar, or the same, emission angle. Moreover, because the first LEDs 202 are arranged closely next to each other and the second LEDs 202b are similarly arranged next to each other, the emission angles associated with each of the LEDs have a large degree of overlap. Similarly, the UVC light 208 emitted by the first LEDs 202a may have a significant degree of overlap with the UVC light emitted by the second LEDs 204b. Although FIG. 2 is shown as a two-dimensional view, it will be understood that the UVC light emitted from each of the LEDs may be a conical light emission, e.g., with a dimension normal to the viewing plane of FIG. 2. In examples, the emission angle may be between about 15° and about 60°, e.g., about a central axis of the emitted light cone.

In the example FIG. 2, the first substrate 204a and the second substrate 204b are generally planar, such that the first LEDs 208 of the second LEDs 202b are disposed on horizontal surfaces. With this arrangement, as shown in FIG. 2, most surfaces associated with the passenger compartment are exposed to the UVC light 208 from the LEDs 202a, 202b. Moreover, because of the close spacing of the LEDs 202 within each of the arrays, and because of the close spacing of the arrays, many surfaces within the seating area 102 are exposed to light from a plurality of the LEDs. This arrangement may result in faster disinfecting times for those surfaces, e.g., as compared to being exposed to the UVC light 208 for only a single LED or relatively fewer LEDs. Moreover, because surfaces with which a passenger will typically interact are relatively farther from the lighting assembly 126, the overlapping of the UVC light 208 of the LEDs 202a, 202b may ensure that enough UVC light 208 is available to effectively eliminate pathogens on those surfaces.

This disclosure is not limited to the arrangement of the LEDs shown in FIG. 2. In other examples, other arrays may be used. For example, and without limitation, the LEDs may be arranged in a 2×2 array. Moreover, the first LEDs 202a and/or the second LEDs 202b may include more or fewer LEDs. The number of LEDs may be selected based on a desired degree of disinfecting, e.g., a percentage of pathogens eliminated, and/or a desired time to achieve the desired degree of disinfection. The number and arrangement of LEDs may also vary based at least in part on a degree and efficacy of active cooling, e.g., from the climate control system 134. Other modifications to the lighting assembly 126 also are contemplated. For example, the first LEDs 202a are disposed on a planar surface provided by the first substrate 204a and the second LEDs 202b are disposed on a planar surface provided by the second substrate 204b. In other examples, one or both of the substrates 204a, 204b may be angled, curved, or otherwise disposed to arrange the LEDs in other than a planar, horizontal array. In one non-limiting example, two or more of the LEDs in the first LEDs 202a may be angled relative to each other. Such an arrangement may provide an increased overall area of coverage for the UVC light 208. Consider the example of FIG. 2 in more detail. As illustrated, peripheral sides 210 of the headrest 104 may not be contacted by the UVC light 208. In one contemplated modification, one of the first LEDs 202a and/or one of the second LEDs 202b may be angled relative to a remainder of the LEDs to purposefully direct UVC light 208 toward the peripheral sides 210 of the headrest 104. Moreover, because the peripheral sides 210 of the headrest 104 are relatively close to the LEDs, light emitted from a single one of the LEDs may be sufficient to eliminate any pathogens from surfaces thereof.

Figure 3:
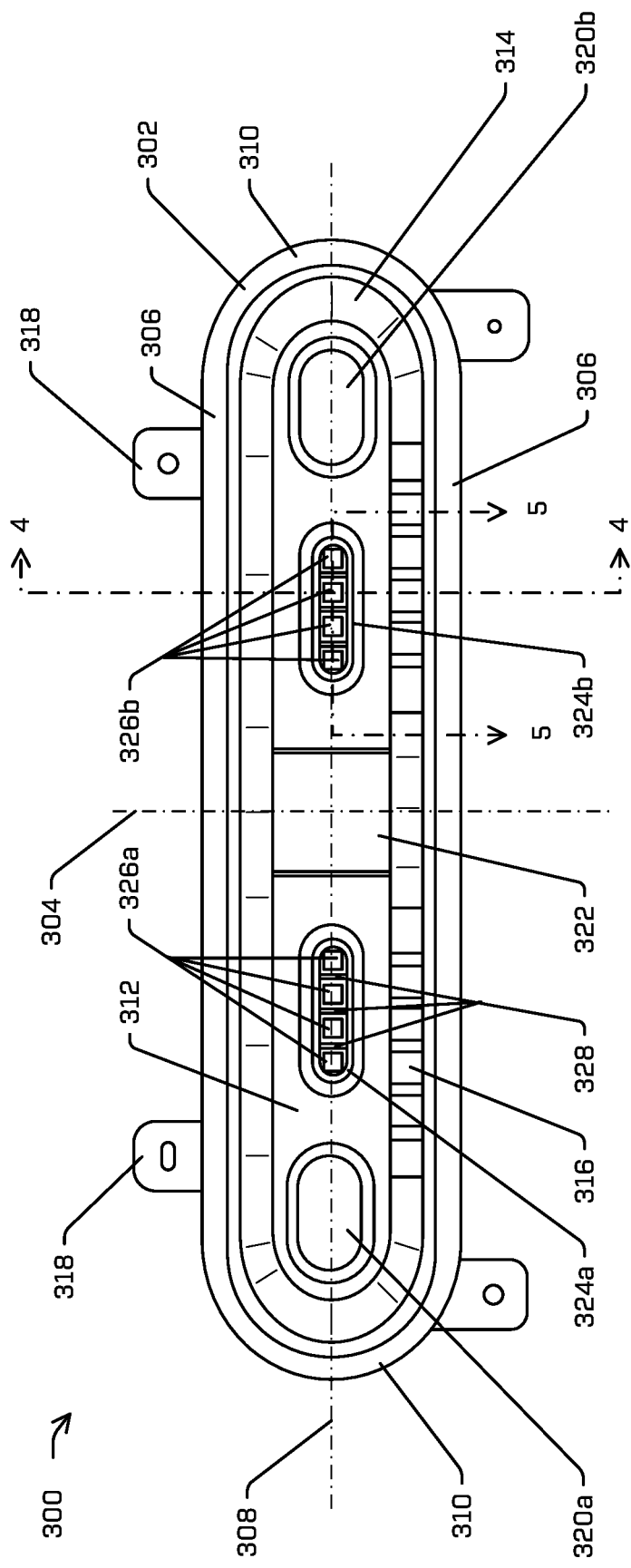
FIG. 3 is a bottom view of the example light assembly shown in FIGS. 1 and 2, as described herein.

FIG. 3 shows an example of a light assembly 300, which may be the light assembly 126 discussed above, in more detail. The light assembly 300 can include a housing 302 configured to retain and support a number of features, as described herein. The housing 302 can be generally elongate, extending laterally, e.g., along a lateral axis 304 between opposing sides 306 and extending longitudinally, e.g., along a longitudinal axis 308, between opposite ends 310. In the example, the sides 306 are generally parallel and straight whereas the opposite ends 310 are generally radiused or arcuate. The sides 306 and the ends 310 generally form a continuous shape about a periphery of the housing 310. The shape of the housing 302 is for example only, as other shapes and configurations will be appreciated from the disclosure and examples described herein.

The housing 302 also includes an interior panel 312 generally circumscribed by the sides 306 and the ends 310. In some examples, a face of the interior panel 312 may be coplanar with a face of the sides 306 and the ends 310, e.g., in the viewing plane of FIG. 3. Alternatively, the interior panel 312 may be recessed relative to the periphery formed by the sides 306 and the ends 310, or the periphery may be recessed relative to the interior panel 312. As detailed further herein, the interior panel 312 may support a number of interactive features, e.g. for interaction by a passenger.

As illustrated, the sides 306 and the ends 310 form a continuous periphery that circumscribes the interior panel 312. Moreover, a gap 314 is formed between the interior panel 312 and the outer periphery formed by the sides 306 and the ends 310. As described further herein, the gap 314 may form part of the passageway through which air, such as temperature-regulated air, may enter the passenger compartment via the housing 302. More specifically, and as illustrated further in FIG. 3, a plurality of vent openings 316 may be formed through a surface within the gap 314. As detailed further herein, the vent openings 316 may be in fluid communication with a source of temperature-regulated forced air or other fluid, such as an HVAC system or the climate control system 134. For instance, a duct or conduit carrying the forced air may be coupled to the housing 302. Stated differently, the gap 314 may be act as a vent, disposed between a central portion of the housing 302 including the inner panel 312 and the outer periphery formed by the sides 306 and the ends 310, via which forced air passes through the housing 302. Although not illustrated in FIG. 3, the housing 302 may further include coverings that can selectively cover the vent openings 316 and/or the gap 314, e.g., to selectively restrict/allow airflow therethrough.

The housing 302 also includes a number of attachment features for securing the housing 302 to an autonomous vehicle. In examples, the housing 302 may be secured proximate a ceiling of an autonomous vehicle, e.g., such that a face of the sides 306 and the ends 310 are generally flush with the ceiling. In the illustrated example, the housing 302 includes a plurality of tabs 318 extending laterally proximate the sides 306. Each of the tabs 316 can include a mounting opening, which may be a hole, a slot, or the like. Although four instances of the tabs 318 are illustrated in FIG. 3, more or fewer of the tabs 318 may be used. Moreover, the tabs 318 are for example only, other mounting features may be included additionally or alternatively. As will be appreciated, the tabs 318 and/or other mounting features may be used to secure the housing 302 relative to the vehicle, e.g., to reframe the vehicle.

As noted above, the interior panel 312 generally provides user interface elements with which a passenger may interact. More specifically, FIG. 3 illustrates a first visible light emitter 320a and a second visible light emitter 320b (collectively, the light emitters 320) integrated into the housing 302 at the interior panel 312. In some instances, the light emitters 320 may be touch-operated, e.g., such that a passenger can selectively illuminate or power off the respective light emitters 320 by touching them or near them. In some examples, the light emitters 320 may comprise a lens or other covering that is contacted by the passenger to selectively illuminate light source and light emitted by the light source may be emitted through the lens. In other examples, the passenger may control illumination of the visible light emitters 320 via an application on an electronic device associated with the passenger, via a separate control within the autonomous vehicle, e.g., via the interactive display 124, or otherwise. In some instances, the light emitters 320 may be controlled directly via computing systems associated with the autonomous vehicle. For example, upon arriving at a location to retrieve a passenger, one or more of the light emitters 320 may be controlled to provide a visual indication to the passenger of an available seat. Also in examples described herein, the light emitters 320 may be controlled to emit visible light at different wavelengths, e.g., to indicate different states of the vehicle. Without limitation, a specific color light or a specific visible light emission pattern may signify that the vehicle is undergoing a disinfecting routine.

An emergency button 322 also is shown in FIG. 3. Specifically, the emergency button 322 is centrally located on the interior panel 312 in the example. The emergency button 322 may be pressed by a passenger to indicate a desire to stop the vehicle. In examples, a vehicle computing system can receive a signal in response to a user pressing the emergency button 322 and execute a safe stop, e.g., by pulling the vehicle to the side of the road or otherwise accessing a safe state/location.

The housing 302 also includes a first opening 324a and a second opening 324b (collectively, the openings 324) space longitudinally on opposite sides of the lateral axis 304. As detailed further herein, the openings 324 may act as windows through which UVC light may be emitted from the housing 302. More specifically, and as also shown in FIG. 3, the housing 302 may retain a plurality of first UVC light-emitting LEDs 326a and a plurality of second UVC light-emitting LEDs 326b. In the illustrated example, the first LEDs 326a are configured to emit light through the first opening 324a and the second LEDs 326b are configured to emit light through the second opening 324b. In examples, the first LEDs 326a may be the first LEDs 202a discussed above in connection with FIG. 2, and/or the second LEDs 326b may be the second LEDs 202b. As with the LEDs 202 discussed above, the first LEDs 326a and the second LEDs 326b (collectively, the LEDs 326, or individually as "an LED 326") may be arranged in arrays, e.g., shown as 1×4 arrays in FIG. 3. As also illustrated in FIG. 3, the housing 302 may include lateral partitions 328 generally extending across the width of the opening 324a, between adjacent ones of the LEDs 326. In some examples, the lateral partitions 328 may be omitted, although the partitions 328 may be desirable to prevent passengers from touching the LEDs 326.

As just described, the lighting assembly 300 includes a number of features and provides various functionalities. For instance, via the gap 314, the lighting assembly 300 provides a vent for climate control within the passenger compartment. Moreover, via the visible light emitters 320, the lighting assembly 300 can provide usable and purposeful illumination within the passenger compartment. Furthermore, the emergency button 322 provides a readily accessible means for user interaction with the vehicle in case of an emergency. In addition, the LEDs 326 provide a source of UVC light for disinfecting the passenger compartment, as described herein. The lighting assembly 300 is for example only, however, and more or fewer of features and functions may be provided in other implementations of the lighting assembly 300. Without limitation, the lighting assembly 300 could further integrate a speaker assembly, a microphone assembly, or other features for interacting with the autonomous vehicle.

Figure 4:
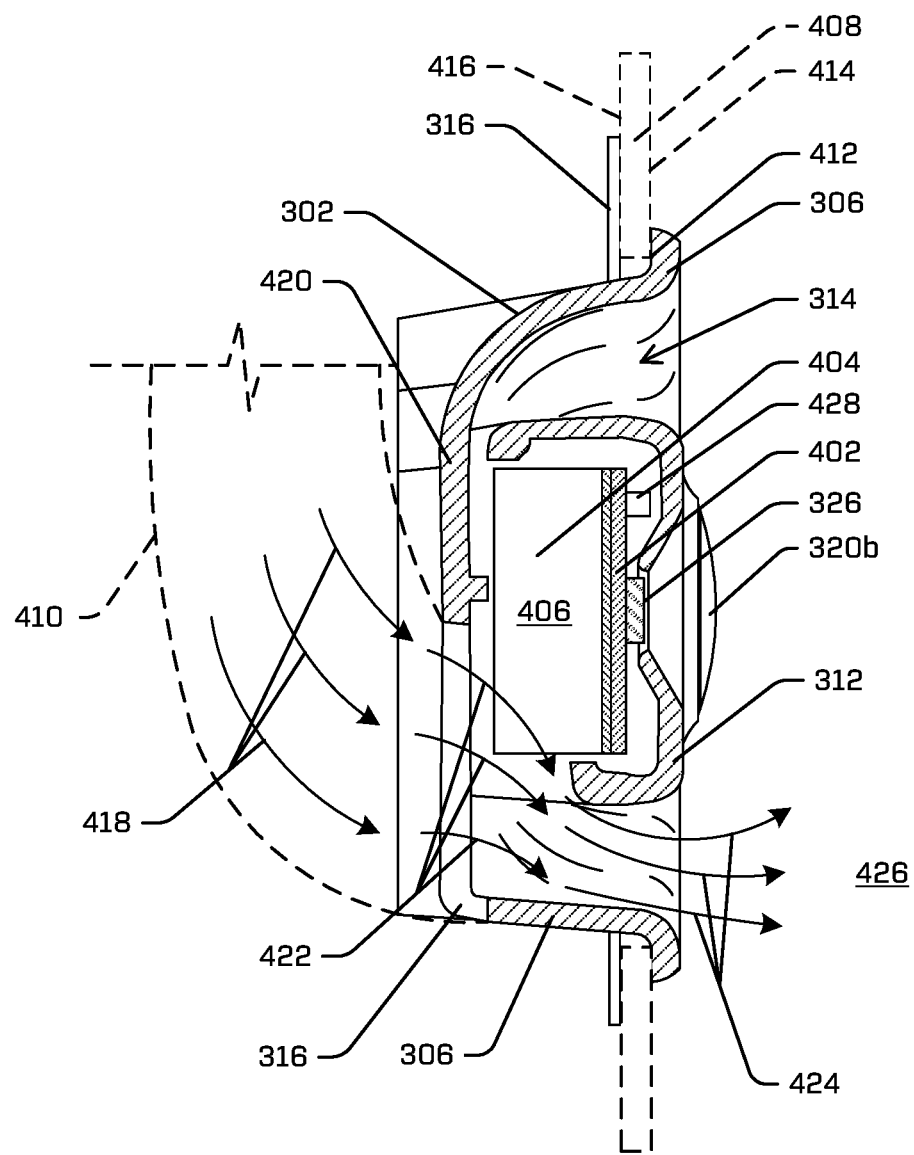
FIG. 4 is a section view of the example light assembly of FIGS. 1, 2, and 3, taken along section line 4-4 in FIG. 3.
Figure 5:
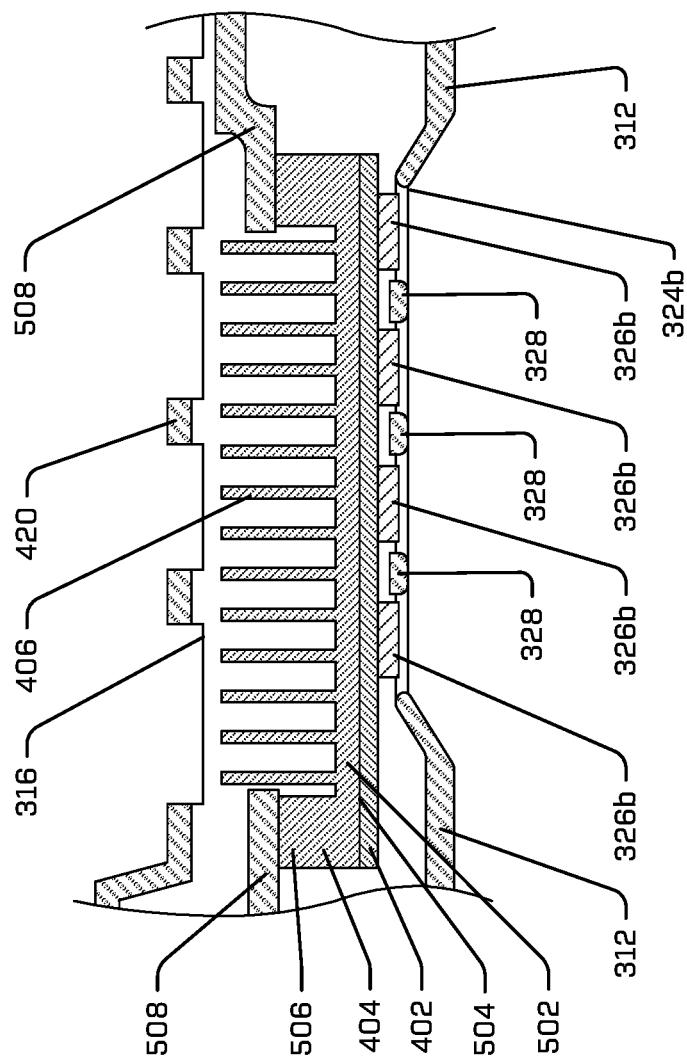
FIG. 5 is a section of view of a portion of the example light assembly of FIGS. 1, 2, and 3, taken along the section line 5-5 in FIG. 3.

Additional aspects of the lighting assembly 300 are shown in more detail in FIGS. 4 and 5, now described. More specifically, FIG. 4 is a cross-section taken along the section line 4-4 in FIG. 3, and FIG. 5 is a cross-sectional view taken along the section line 5-5 in FIG. 3. For ease of understanding, elements introduced in FIG. 3 and discussed above are given the same reference numerals in FIGS. 4 and 5.

FIG. 4 is a cross-sectional view taken generally normal to the longitudinal axis 308. As shown in FIG. 4, an LED 326 of the second LEDs 326b is disposed on a substrate 402. In examples, the substrate 402 may be the same as or similar to the substrate 204 discussed above. The substrate 402 may be a printed circuit board, e.g., a PCBA, and/or other type of substrate. In examples, the substrate 402 may be coupled to a power source and may supply power from the power source to the LED 326. Although the substrate 402 is illustrated as being substantially planar, other implementations of the substrate may be curved, angled, or otherwise configured. As shown in FIG. 4, the LED 326, as with all of the second LEDs 326b may be disposed directly on, e.g., integrated into, the substrate 402, although in some examples, the substrate and the LED 326 be may be otherwise coupled.

FIG. 4 also illustrates a heat sink 404 disposed on a side of the substrate 402 opposite a side on which the LED 326 is disposed. As will be appreciated, UVC-emitting LEDs generate relatively large amounts of thermal energy, and as will also be appreciated, coupling multiple of the LEDs 326b on the same substrate 402 can provide sufficient thermal energy to negatively impact the substrate 402 and/or surrounding components. For instance, the thermal energy may deform the substrate 402 and/or portions of the housing 302 proximate the LEDs 326. In extreme cases, the thermal energy may be sufficient to melt the substrate 402 and/or the housing 302. The heat sink 404 is provided to help dissipate this thermal energy. In the example illustrated, the heat sink 404 includes a plurality of fins 406 (of which a single fin 406 is shown) and is coupled to the substrate 402. In other implementations, the heat sink 404 may be otherwise configured and/or arranged to distribute the thermal load generated by the LEDs 326. Without limitation, the heat sink 404 may be formed of a highly conductive material, such as aluminum, copper, or the like.

In addition to illustrating the housing 302, FIG. 4 shows environment of the housing 302, including an example ceiling 408 and an example duct 410. As also shown, the housing 302 may be configured to abut or otherwise connect to the ceiling 408. In the illustrated example, the sides 306 of the housing 302 may be configured as flanges that define a rear, flanged surface 412 configured to contact a face 414 of the ceiling 408. As also shown in FIG. 4, the tabs 316 may contact a rear surface 416 of the ceiling 408, e.g., opposite the face 414 contacted by the flanged surface 412. Of course, the example interface of the housing 302 with the ceiling 408 is for example only. Other configurations are contemplated. For instance, and without limitation, the housing 302 may be configured such that the sides 306 are disposed on an opposite side of the ceiling 408 than what is illustrated. Stated differently, the sides 306 of the housing 302 may be disposed within, or above, the ceiling 408. Other configurations also will be appreciated by those having ordinary skill in the art, with the benefit of this disclosure.

The duct 410 is an example conduit via which forced air may be received proximate the housing 302, e.g., from a climate control system, such as the climate control system 134 discussed above. FIG. 4 also shows the flow of air from the duct 410 according to aspects of this disclosure. More specifically, FIG. 4 illustrates first arrows 418 generally showing the flow of temperature-regulated, forced air through the duct 410. The duct 410 is in fluid communication with the housing 302, e.g., in contact with a rear surface 420 of the housing 302 and/or one or more of the sides 306 (and/or the ends 310) of the housing 302.

As illustrated by second arrows 422, the temperature-regulated air enters the housing 302, from the duct 410, via the vent openings 316. As also shown, as the air enters the housing, a portion of the airflow passes over the fins 406 of the heat sink 404. According to implementations of this disclosure, the heat sink 404 is integrated into the lighting assembly 300 to be at least partially in the flow of the temperature-regulated air. As will be appreciated, the airflow represented by the second arrows 422 may help to remove heat from the heat sink 404, thereby dissipating heat generated by the LEDs 326. As shown by the third arrows 424, the forced air may further pass through the housing 302, e.g., via the gap 314, into a passenger compartment 426. Although not shown in the example of FIG. 4, the housing 302 may also include one or more diverters or similar features, e.g., disposed in the gap 314, to route air differently through the gap 314. In some examples, such diverters may force some of the airflow represented by the second arrows 422 and/or the third arrows 424 in a direction perpendicular to the viewing plane of FIG. 4. The diverters can disperse air from the duct 410 in different directions. In other examples, the vent openings 316 may have angled sides that direct airflow in different directions.

In example processes described herein, when the LEDs 326 are operated to disinfect a passenger compartment, the climate control system of the vehicle may be configured to pass cool air through the duct 410 to improve dissipation of thermal energy generated by the LEDs 326. As also described herein, the temperature of the air may be regulated based on a thermal load proximate the LEDs 326. FIG. 4 also illustrates a temperature sensor 428 configured to sense a temperature proximate the LEDs 326 to facilitate such temperature regulation. The temperature sensor 428 is disposed on the substrate 402 in FIG. 4, although in other examples the temperature sensor 428 may be otherwise disposed in the housing 302. In at least some examples, the temperature sensor 428 may be a thermistor 428 integrated into the substrate 402.

FIG. 5 shows additional aspects of the light assembly 300. For instance, FIG. 5 better illustrates the heat sink 404, including the fins 406. The fins 406 generally comprise a plurality of planar protrusions extending from a support 502, in a direction away from the substrate 402. The support 502 has a generally planar surface 504 that abuts the substrate 402, with the fins extending from a surface opposite the planar surface 504. Lateral ends 506 of the heat sink 404 may be secured to mounting structures 508, e.g., to retain the heat sink 404, substrate 402, and LEDs 326 in the housing 302. Without limitation, the mounting structures 508 may be integrally formed with the housing and the heat sink 404 may be fastened thereto using conventional fasteners, such as screws, bolts, rivets, or the like (omitted from FIG. 5 for clarity). The configuration of the heat sink, including the number and arrangement of the fins 406, is for example only; other configurations may be used.

FIG. 5 also demonstrates the dividing of the opening 324b by the lateral partitions 328. In this example, the lateral partitions 328 are disposed between the LEDs 326b, e.g., so as to not interfere with the UVC light emitted by the LEDs 326b. The emitted UVC light exits the housing 302 unobstructed. In other examples, a lens or other element may be disposed over the opening 324b or a portion of the opening 324b. For example, lenses may be used to refract, reflect, diffuse, or otherwise alter a path of the UVC light emitted by the LEDs 326b. As will be appreciated, UVC light is readily absorbed by most surface, so any lenses or coverings may be made of quartz, which does not absorb UVC-light. In still other examples, and although not illustrated in FIGS. 3-5, the lighting assembly 300 may further include a cover, such as a retractable or removable cover that covers the UVC light-emitting LEDs 326a, 326b when not in use. Such a cover may be a safety feature that ensure UVC light is not emitted into the passenger compartment other than during a disinfecting routine.

Although FIGS. 4 and 5 specifically illustrate details of the second LEDs 326b, details of the first LEDs 326a may be substantially the same or, in some instances, identical.

Figure 6:
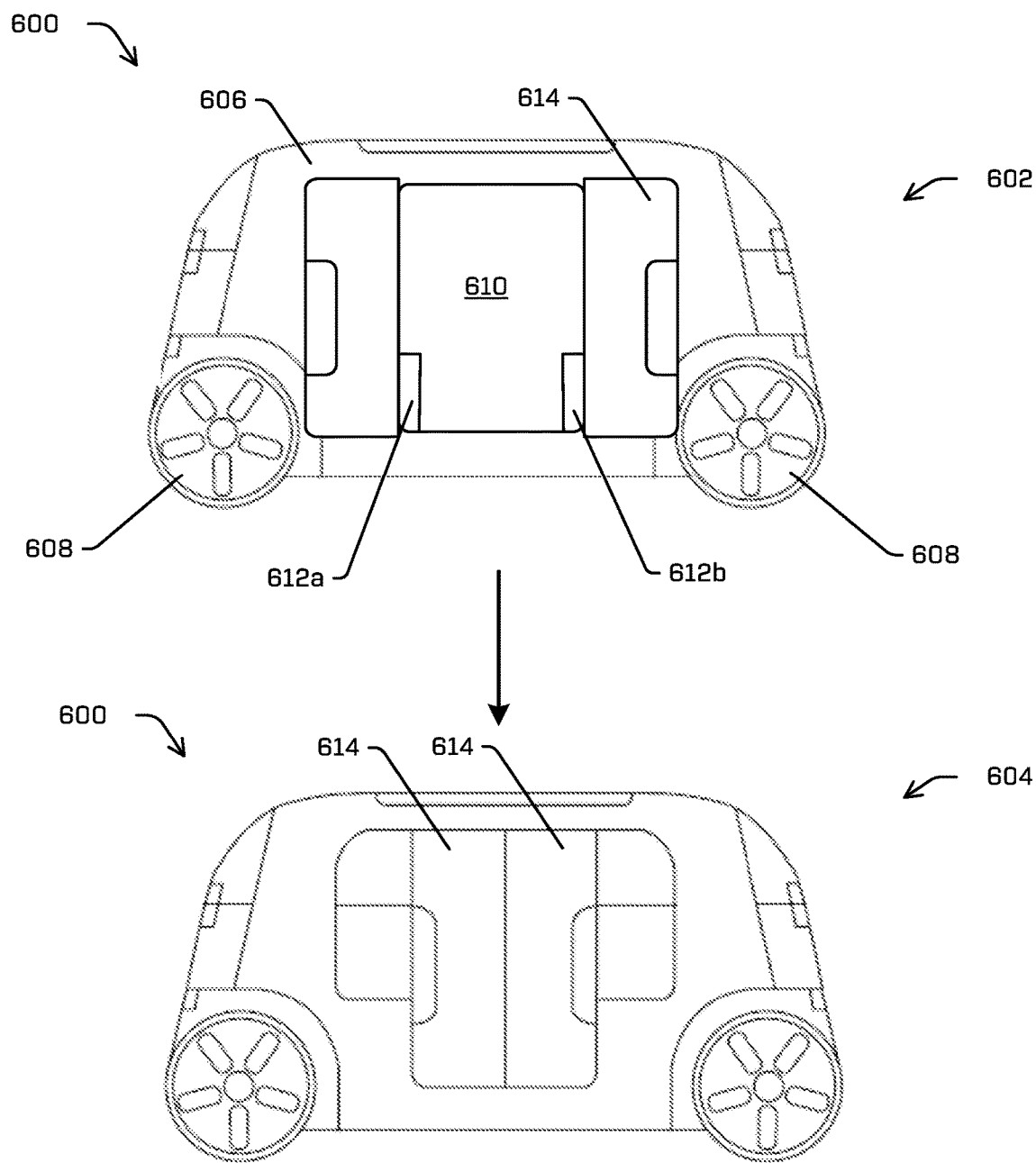
FIG. 6 is a schematic illustration showing an autonomous vehicle in first and second configurations, according to aspects of this disclosure.

As noted above, the lighting assembly 300 may be particularly useful in vehicles, including autonomous vehicles. FIG. 6 illustrates an example autonomous vehicle 600 with which the light assembly 300 may be used. However, the lighting assembly 300 is not limited to use in the autonomous vehicle 600 and the autonomous vehicle 600 may not require the lighting assembly 300.

In more detail, FIG. 6 illustrates the autonomous vehicle 600 in a first configuration 602 and a second configuration 604. Generally, the autonomous vehicle includes a body 606 and a plurality of wheels 608 for transporting the vehicle 600 along a surface, e.g., a road. As will be appreciated, the vehicle 600 is not limited to the shape of the body 606 illustrated. In other instances, the body may take the shape of a conventional sedan, SUV, bus, or the like. Moreover, the vehicle 600 is not limited to including the wheels 608. In other examples, tracks or the like may be used instead of the wheels 608. More or fewer wheels than those illustrated may also be used.

The body 606 generally defines a passenger compartment 610 in which passengers may be transported by the vehicle 600. In the example, a first seating area 612a and a second seating area 612b (only a portion of which are shown) are provided in the passenger compartment 610. In examples, the first seating area 612a and the second seating area 612b may correspond to instances of the seating area 102 discussed above. In the illustrated example, the first seating area 612a and the second seating area 612b are arranged to face each other, e.g., in a carriage-style arrangement with the passenger(s) in the first seating area 612a facing the passenger(s) in the second seating area 612b. Seating within the passenger compartment 610, including the number and direction of seats, is not limited to the illustrated seating arrangement.

Although not visible in FIG. 6, a lighting assembly, like the lighting assembly 126 and/or the lighting assembly 300 may be disposed to emit UVC light into the passenger compartment 610, e.g., according to implementations and techniques described herein. In some examples, a first instance of a lighting assembly may be provided above the first seating area 612a and a second instance of the light assembly may be provided above the second seating area 612b. In other examples, UVC light emitters may be disposed other than in a lighting assembly, but may nonetheless be controlled according to techniques described herein.

FIG. 6 also illustrates two doors 614 movable between an open position in the first configuration 602 and a closed position in the second configuration 604. More specifically, in the first configuration 602, the doors 614 are configured to allow passenger ingress into and egress out of the passenger compartment 610. In the second configuration 604, the doors 614 prevent passenger ingress/egress. In some examples described herein, the doors 614 in the second configuration 604 may be locked or otherwise secured, e.g., to prevent the doors 614 from opening during a disinfecting routine that includes emission of UVC-light. Although the illustrated autonomous vehicle 600 shows two doors 614, e.g., two panels separately movable relative to the body 606, more or fewer doors may be used.

In examples of this disclosure, the lighting assemblies 126, 300 may provide unique benefits to implement aspects of UVC light disinfecting. For instance, the lighting assemblies 126, 300 may position UVC light emitters in a desirable position for effective disinfecting of those surfaces most often exposed to pathogens. Moreover, because the lighting assemblies 126, 300 can include aspects of a climate control system, the lighting assemblies 126, 300 can provide active cooling of the UVC light emitters. Conventionally available UVC light-emitting LEDs provide a smaller device that may be readily implemented in smaller spaces, such as spaces available in the lighting assemblies 126, 300, but these LEDs generate large amounts of heat. Without the active cooling provided by the lighting assemblies 126, 300 described herein, such LEDs may not be practical for use in autonomous vehicle applications. At the very least, the number of LEDs required to disinfect a passenger compartment in a desirable disinfecting time may generate too much heat for practical use, absent the active cooling described herein. In at least some examples, the number and arrangement of UVC light-emitting LEDs may be selected to expose surfaces to be disinfected up to about 50 $J/m^2$ of radiation, which may correlate to elimination of about 99.9% of bacteria. In examples, the LED arrangements described herein may obtain this level of radiation in about 10 minutes or less.

Figure 7:
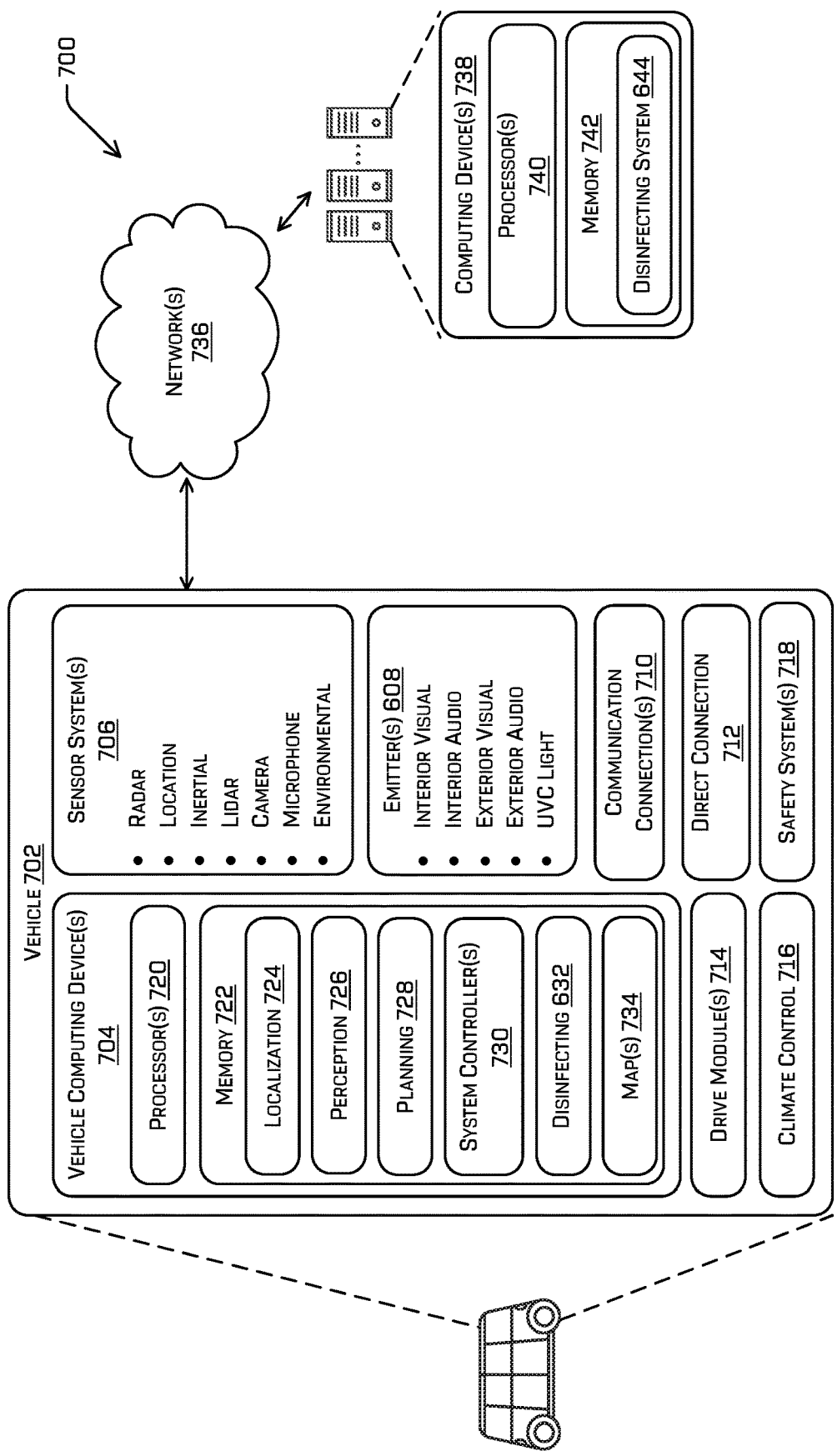
FIG. 7 depicts a block diagram of an example system for implementing the techniques described herein.

FIG. 7 illustrates a block diagram of an example system 700 for implementing the techniques described herein. In at least one example, the system 700 can include a vehicle 702 of which the portion 100 described above with reference to FIG. 1 is a part. The vehicle 702 may be the vehicle 600.

The vehicle 702 can include a vehicle computing device 704, one or more sensor systems 706, one or more emitters 708, one or more communication connections 710, at least one direct connection 712, one or more drive modules 714, a climate control system 716, and one or more safety systems 718.

The vehicle computing device 704 can include one or more processors 720 and memory 722 communicatively coupled to the processor(s) 720. In the illustrated example, the vehicle 702 is an autonomous vehicle; however, the vehicle 702 can be any other type of vehicle. Moreover, the techniques described herein are not limited to vehicles, and can be used in other sensing environment. In the illustrated example, the memory 722 of the vehicle computing device(s) 704 stores a localization component 724, a perception component 726, a planning component 728, and one or more system controllers 730. The memory 722 also stores a disinfecting system 732 and one or more maps 734. Though depicted in FIG. 7 as residing in the memory 722 for illustrative purposes, it is contemplated that several of the features, including aspects of the disinfecting system 732, the map(s) 734, and/or other components may additionally, or alternatively, be accessible to the vehicle 702 (e.g., stored remotely).

In at least one example, the localization component 724 can include functionality to receive data from the sensor system(s) 706 to determine a position of the vehicle 702. For example, the localization component 724 can include, request, and/or receive a three-dimensional map of an environment and can continuously determine a location of the vehicle 702 within the map. In some instances, the localization component 724 can utilize SLAM (simultaneous localization and mapping) or CLAMS (calibration, localization and mapping, simultaneously) to receive image data, LIDAR data, radar data, SONAR data, IMU data, GPS data, wheel encoder data, and/or the like to accurately determine a location of the vehicle 702. In some instances, the localization component 724 can provide data to various components of the vehicle 702 to determine an initial position of the vehicle 702 for generating a candidate trajectory.

In some instances, the perception component 726 can include functionality to perform object detection, segmentation (e.g., semantic segmentation), and/or classification. The perception component 726 can be substantially the same as, and/or include functionality described above in connection with, the perception system 112. In some examples, the perception component 726 can provide processed sensor data that indicates a presence of an entity that is proximate to the vehicle 702 and/or a classification of the entity as an entity type (e.g., articulated object, car, pedestrian, cyclist, animal, tree, road surface, curb, sidewalk, lamppost, signpost, unknown, etc.). In implementations, the perception component can specifically identify articulated objects, such as articulated vehicles, and generate estimated state information for each of a plurality of segments comprising a representation of the articulated object. In additional and/or alternative examples, the perception component 726 can provide processed sensor data that indicates one or more characteristics associated with a detected entity and/or the environment in which the entity is positioned. In some examples, characteristics associated with an entity can include, but are not limited to, an x-position (global position), a y-position (global position), a z-position (global position), an orientation, an entity type (e.g., a classification), a velocity of the entity, an extent of the entity (e.g., size), one or more yaw angles associated with the entity, one or more yaw rates associated with the entity, etc. Characteristics associated with the environment can include, but are not limited to, a presence of another entity in the environment, a state of another entity in the environment, a time of day, a day of a week, a season, a weather condition, an indication of darkness/light, etc.

The planning component 728 can determine a path for the vehicle 702 to follow to traverse through an environment. For example, the planning component 728 can determine various routes and trajectories and various levels of detail. The planning component 728 may determine a route to travel from a first location (e.g., a current location) to a second location (e.g., a target location). For the purpose of this discussion, a route can be a sequence of waypoints for travelling between the two locations. As non-limiting examples, waypoints can include streets, intersections, global positioning system (GPS) coordinates, etc. Further, the planning component 728 can generate an instruction for guiding the autonomous vehicle along at least a portion of the route from the first location to the second location. In at least one example, the planning component 728 can determine how to guide the autonomous vehicle from a first waypoint in the sequence of waypoints to a second waypoint in the sequence of waypoints. In some examples, the instruction can be a trajectory, or a portion of a trajectory. Also in some examples, multiple trajectories can be substantially simultaneously generated (e.g., within technical tolerances) in accordance with a receding horizon technique. In examples of this disclosure, the planning component 728 can also determine estimated travel times, e.g., to travel from a current location to a destination. For instance, the planning component 728 can generate travel paths that will take longer than a disinfection time associated with the disinfecting system 732, as described herein.

The system controller(s) 730 can be configured to control steering, propulsion, braking, safety, emitters, communication, and other systems of the vehicle 702. The system controller(s) 730 can communicate with and/or control corresponding systems of the drive module(s) 714 and/or other components of the vehicle 702. In examples of this disclosure, the system controller(s) 730 can control the climate control system 716 and/or the safety system(s) 718, e.g., based on instructions from the disinfecting system 732.

The disinfecting system 732 includes functionality to disinfect a passenger compartment of the vehicle 702 using UVC-light, as detailed herein. The disinfecting system 732 can include instructions for causing the UVC light emitters to emit UVC light for a predetermined amount of time, e.g. a disinfecting time or an exposure time. In examples, the disinfecting system 732 can receive information from the planning system 728 to determine whether the disinfecting time is shorter than a time to a next access of the vehicle by a passenger. For instance, after the vehicle 702 drops off passengers, the planning system 728 may determine a next destination, e.g., to retrieve a next passenger. The planning system 728 may also determine a time to traverse to the next destination. The disinfecting system 732 may receive this transit time, and determine whether the vehicle interior can be disinfected, e.g., based on a comparison of the transit time to the disinfecting time. In examples, the planning system 728 may be configured to choose a next destination to which the transit time will purposefully exceed the disinfecting time. For instance, after some predetermined time in use, number of rides, number of passengers, or the like, the planning system 728 may prioritize disinfecting the passenger compartment.

The disinfecting system 732 can also generate signals to cause the system controller(s) 730 to perform certain actions in the vehicle 702 to carry out the disinfecting routine. Such actions may include emitting UVC-light, securing the vehicle 700 to prevent ingress of passengers, controlling visible light and/or audio emitters to indicate that disinfecting is in progress, or the like. In examples, the disinfecting system 732 can also receive temperature information, as described herein, to control the climate control system 716 to increase heat transfer away from the UVC light emitters, a substrate carrying the UVC light emitters, and/or a heat sink associated therewith.

In some examples, the disinfecting system 732 can store or otherwise access a number of disinfecting routines or processes. For example, the disinfecting system 732 can store routine specific to different types of disinfecting. In some examples, when more time is available for disinfecting, a routine that uses fewer than all of the UVC light emitters may be used for a longer period of time, e.g., to reduce power consumption or the like. Moreover, different routines may target different portions of the interior of the vehicle 702. For instance, if it is determined that passengers and/or cargo have only been in certain seats within the vehicle 702, a disinfecting routine may be selected to disinfect only those seats that have been occupied and/or to more thoroughly disinfect those seats. In other examples, different routines may correlate to a desired amount of disinfecting. For instance, surfaces may be disinfected to a greater degree with longer exposure to UVC-light, but some disinfection may take place at shorter exposure times. Thus, routines stored in association with the disinfecting system 732 can include different predetermined times, and may result in different degrees of disinfection/cleaning.

The map(s) 734 can include one or more maps of an environment of the autonomous vehicle 702. In examples, the localization component 724 and/or the planning component map(s) 734 can use the map(s) 734 to determine a current location of the vehicle 702, a destination for the vehicle 702, and/or other spatial information. For instance, the map(s) 734 may be used to determine a transit time to a destination and/or identify a next destination that will allow for adequate time to disinfect the vehicle prior to a next passenger enter the vehicle 702.

In some instances, aspects of some or all of the components discussed herein may include any models, algorithms, and/or machine learning algorithms. For example, in some instances, the components in the memory 722 (and memory 742, discussed below) may be implemented as a neural network.

As described herein, an exemplary neural network is a biologically inspired algorithm which passes input data through a series of connected layers to produce an output. Each layer in a neural network may also comprise another neural network, or may comprise any number of layers (whether convolutional or not). As may be understood in the context of this disclosure, a neural network may utilize machine learning, which may refer to a broad class of such algorithms in which an output is generated based on learned parameters.

Although discussed in the context of neural networks, any type of machine learning may be used consistent with this disclosure. For example, machine learning algorithms may include, but are not limited to, regression algorithms (e.g., ordinary least squares regression (OLSR), linear regression, logistic regression, stepwise regression, multivariate adaptive regression splines (MARS), locally estimated scatterplot smoothing (LOESS)), instance-based algorithms (e.g., ridge regression, least absolute shrinkage and selection operator (LASSO), elastic net, least-angle regression (LARS)), decisions tree algorithms (e.g., classification and regression tree (CART), iterative dichotomiser 7 (ID3), Chi-squared automatic interaction detection (CHAID), decision stump, conditional decision trees), Bayesian algorithms (e.g., naïve Bayes, Gaussian naïve Bayes, multinomial naïve Bayes, average one-dependence estimators (AODE), Bayesian belief network (BNN), Bayesian networks), clustering algorithms (e.g., k-means, k-medians, expectation maximization (EM), hierarchical clustering), association rule learning algorithms (e.g., perceptron, back-propagation, hopfield network, Radial Basis Function Network (RBFN)), deep learning algorithms (e.g., Deep Boltzmann Machine (DBM), Deep Belief Networks (DBN), Convolutional Neural Network (CNN), Stacked Auto-Encoders), Dimensionality Reduction Algorithms (e.g., Principal Component Analysis (PCA), Principal Component Regression (PCR), Partial Least Squares Regression (PLSR), Sammon Mapping, Multidimensional Scaling (MDS), Projection Pursuit, Linear Discriminant Analysis (LDA), Mixture Discriminant Analysis (MDA), Quadratic Discriminant Analysis (QDA), Flexible Discriminant Analysis (FDA)), Ensemble Algorithms (e.g., Boosting, Bootstrapped Aggregation (Bagging), AdaBoost, Stacked Generalization (blending), Gradient Boosting Machines (GBM), Gradient Boosted Regression Trees (GBRT), Random Forest), SVM (support vector machine), supervised learning, unsupervised learning, semi-supervised learning, etc.

Additional examples of architectures include neural networks such as ResNet30, ResNet101, VGG, DenseNet, PointNet, and the like.

The sensor system(s) 706 can include one or more of LiDAR sensors, radar sensors, time-of-flight sensors, ultrasonic transducers, SONAR sensors, location sensors (e.g., GPS, compass, etc.), inertial sensors (e.g., inertial measurement units, accelerometers, magnetometers, gyroscopes, etc.), cameras (e.g., RGB, IR, intensity, depth, time of flight, etc.), microphones, wheel encoders, environment sensors (e.g., temperature sensors, humidity sensors, light sensors, pressure sensors, etc.), presence/absence sensors, weight or mass detectors, etc. The sensor system(s) 706 can include multiple instances of each of these or other types of sensors. For instance, the LIDAR sensors (and/or radar sensors) can include individual LIDAR sensors (or radar sensors) located at the corners, front, back, sides, and/or top of the vehicle 702. As another example, the camera sensors can include multiple cameras disposed at various locations about the exterior and/or interior of the vehicle 702. The sensor system(s) 706 can provide input to the vehicle computing device 704. For instance, and without limitation, the sensor system(s) 706 can provide images of an interior of the vehicle 702, e.g., of a passenger compartment of the vehicle 702, which images may be used to determine whether occupants are present in the passenger compartment. The sensor system(s) 706 can also include other presence sensors, mass-detection sensors, thermal imagers, or the like, to generate additional (or alternative) data to determine passenger presence. Also in examples of this disclosure, the sensor system(s) 706 can include a temperature sensor, e.g., a thermistor, to determine a temperature proximate UVC light-emitting LEDs, a substrate coupled to the LEDs, and/or a heat sink thermally coupled to the LEDs and/or the substrate. Additionally, or alternatively, the sensor system(s) 706 can send sensor data, via one or more networks 736, to one or more remote computing devices at a particular frequency, after a lapse of a predetermined period of time, in near real-time, etc.

The emitter(s) 708 can include structure and functionality for emitting light and/or sound. In examples, the emitter(s) 708 can include the UVC light emitters discussed herein. For instance, the UVC light emitters may be embodied as light-emitting diodes (LEDs), as detailed herein. The emitter(s) 708 can also include interior audio and visual emitters to communicate with passengers or would-be passengers of the vehicle 702. By way of example and not limitation, interior emitters can include speakers, lights, signs, display screens, touch screens, haptic emitters (e.g., vibration and/or force feedback), mechanical actuators (e.g., seatbelt tensioners, seat positioners, headrest positioners, etc.), and the like. The emitter(s) 708 can also include exterior emitters. By way of example and not limitation, the exterior emitters in this example can include lights to signal a direction of travel or other indicator of vehicle action (e.g., indicator lights, signs, light arrays, etc.), and one or more audio emitters (e.g., speakers, speaker arrays, horns, etc.) to audibly communicate with pedestrians or other nearby vehicles, one or more of which comprising acoustic beam steering technology. In examples of this disclosure, the audible emitters and/or visible light emitters can be configured to indicate a status of the vehicle 702, e.g., a first status associated with a disinfecting state of the vehicle (in which passengers are not permitted ingress into the vehicle 702) and a second status associated with a normal state of operation of the vehicle (in which passengers may be permitted ingress into the vehicle 702).

The communication connection(s) 710 can enable communication between the vehicle 702 and one or more other local or remote computing device(s). For instance, the communication connection(s) 710 can facilitate communication with other local computing device(s) on the vehicle 702 and/or the drive module(s) 714. In one non-limiting example, the communication connection(s) 710 can facilitate communication between the disinfecting system 732 and the system controller(s) 730, e.g., so the system controller(s) 730 can implement disinfecting functionality, as detailed herein. Also, the communication connection(s) 710 can allow the vehicle to communicate with other nearby computing device(s) (e.g., other nearby vehicles, traffic signals, etc.). The communications connection(s) 710 also enable the vehicle 702 to communicate with a remote teleoperations computing device or other remote services.

The communication connection(s) 710 can include physical and/or logical interfaces for connecting the vehicle computing device 704 to another computing device or a network, such as the network(s) 736. For example, the communications connection(s) 710 can enable Wi-Fi-based communication such as via frequencies defined by the IEEE 802.11 standards, short range wireless frequencies such as Bluetooth, cellular communication (e.g., 2G, 3G, 4G, 4G LTE, 5G, etc.) or any suitable wired or wireless communications protocol that enables the respective computing device to interface with the other computing device(s).

The drive module(s) 714 can include many of the vehicle systems, including a high voltage battery, a motor to propel the vehicle 702, an inverter to convert direct current from the battery into alternating current for use by other vehicle systems, a steering system including a steering motor and steering rack (which can be electric), a braking system including hydraulic or electric actuators, a suspension system including hydraulic and/or pneumatic components, a stability control system for distributing brake forces to mitigate loss of traction and maintain control, an HVAC system, lighting (e.g., lighting such as head/tail lights to illuminate an exterior surrounding of the vehicle), and one or more other systems (e.g., cooling system, safety systems, onboard charging system, other electrical components such as a DC/DC converter, a high voltage junction, a high voltage cable, charging system, charge port, etc.). Additionally, the drive module(s) 714 can include a drive module controller which can receive and preprocess data from the sensor system(s) and to control operation of the various vehicle systems. In some examples, the drive module controller can include one or more processors and memory communicatively coupled with the one or more processors. The memory can store one or more modules to perform various functionalities of the drive module(s) 714. Furthermore, the drive module(s) 714 also include one or more communication connection(s) that enable communication by the respective drive module with one or more other local or remote computing device(s).

In some examples, the drive module(s) 714 may be a single drive module 714. In at least one example, if the vehicle 702 has multiple drive modules 714, individual drive modules 714 can be positioned on opposite ends of the vehicle 702 (e.g., the front and the rear, etc.). In at least one example, the drive module(s) 714 can include one or more sensor systems to detect conditions of the drive module(s) 714 and/or the surroundings of the vehicle 702. By way of example and not limitation, the sensor system(s) 706 can include one or more wheel encoders (e.g., rotary encoders) to sense rotation of the wheels of the drive modules, inertial sensors (e.g., inertial measurement units, accelerometers, gyroscopes, magnetometers, etc.) to measure orientation and acceleration of the drive module, cameras or other image sensors, ultrasonic sensors to acoustically detect objects in the surroundings of the drive module, LIDAR sensors, radar sensors, etc. Some sensors, such as the wheel encoders can be unique to the drive module(s) 714. In some cases, the sensor system(s) on the drive module(s) 714 can overlap or supplement corresponding systems of the vehicle 702 (e.g., the sensor system(s) 706).

In the illustrated example, the climate control system 716 and the safety system 718 are shown as separate from the drive module(s) 714, but in examples either or both of these components may be included in the drive module(s) 714.

The climate control system 716 may be the climate control system 134 discussed above. For instance, and without limitation, the climate control system 716 can include one or more conduits or ducts that direct forced air into a passenger compartment of the vehicle 702. The climate control system 716 can also include a temperature regulation system for controlling the temperature of the force air. For instance, the climate control system 716 can include elements of an HVAC system, including, but not limited to, an evaporator, a compressor, and/or a condenser, e.g., as a cooling system, and/or a heating element, e.g., as a heating system. In examples, the climate control system 716 can be controlled by the system controller(s) 730 and/or the disinfecting system 732, e.g., to lower a temperature of forced air passing across a heat sink to dissipate heat generated by UVC light-emitting LEDs, as described herein.

The safety system(s) 718 can include systems of the vehicle 702 that can be used to ensure safe operation during a disinfecting cycle. Without limitation, the safety system(s) 718 can be used to configure the vehicle in a configuration that prevents ingress into the passenger compartment during operation of the UVC light-emitting LEDs. For example, the safety system(s) 718 can include one or more actuators that "lock" or otherwise prevent opening of doors or other ingress/egress coverings for the duration of a disinfecting cycle. In other examples, the safety system(s) 718 can include coverings or the like that may selectively shield windows and/or other components from UVC light during a disinfecting regimen. The safety system(s) 718 can work in concert with the emitter(s) 708 to ensure that disinfection using the UVC light emitters poses no threat to passengers.

The processor(s) 720 of the vehicle 702 can be any suitable processor capable of executing instructions to process data and perform operations as described herein. By way of example and not limitation, the processor(s) 720 can comprise one or more Central Processing Units (CPUs), Graphics Processing Units (GPUs), or any other device or portion of a device that processes electronic data to transform that electronic data into other electronic data that can be stored in registers and/or memory. In some examples, integrated circuits (e.g., ASICs, etc.), gate arrays (e.g., FPGAs, etc.), and other hardware devices can also be considered processors in so far as they are configured to implement encoded instructions.

The memory 722 is an example of non-transitory computer-readable media. The memory 722 can store an operating system and one or more software applications, instructions, programs, and/or data to implement the methods described herein and the functions attributed to the various systems. In various implementations, the memory can be implemented using any suitable memory technology, such as static random-access memory (SRAM), synchronous dynamic RAM (SDRAM), nonvolatile/Flash-type memory, or any other type of memory capable of storing information. The architectures, systems, and individual elements described herein can include many other logical, programmatic, and physical components, of which those shown in the accompanying figures are merely examples that are related to the discussion herein.

While FIG. 7 is illustrated as a distributed system, in alternative examples, components of the vehicle 702 can be associated with remote computing devices accessible via the network(s) 736. For example, the vehicle 702 can send sensor data to one or more computing devices 738, via the network(s) 736. In some examples, the vehicle 702 can send raw sensor data to the computing device(s) 738. In other examples, the vehicle 702 can send processed sensor data and/or representations of sensor data to the computing device(s) 738. In some examples, the vehicle 702 can send sensor data to the computing device(s) 738 at a particular frequency, after a lapse of a predetermined period of time, in near real-time, etc. In some cases, the vehicle 702 can send sensor data (raw or processed) to the computing device(s) 738 as one or more log files.

The computing device(s) 738 can receive the sensor data (raw or processed), and/or representations generated based on the sensor data, and can perform operations on the data. In at least one example, the computing device(s) 738 can include one or more processors 740 and memory 742 communicatively coupled to the processor(s) 740. In the illustrated example, the memory 742 of the computing device(s) 738 stores a disinfecting system 744. The disinfecting system 744 can include functionality to perform operations similar to some or all of those discussed above in the context of the disinfecting system 732. For instance, scheduling of pickups and drop offs may be handled remotely, e.g., for a fleet, to optimize or allow time for disinfecting of the vehicle 702. In some instances, the processor(s) 740 and the memory 742 can include functionality and/or structure similar to that discussed above with respect to the processor(s) 720 and the memory 722.

Figure 8:
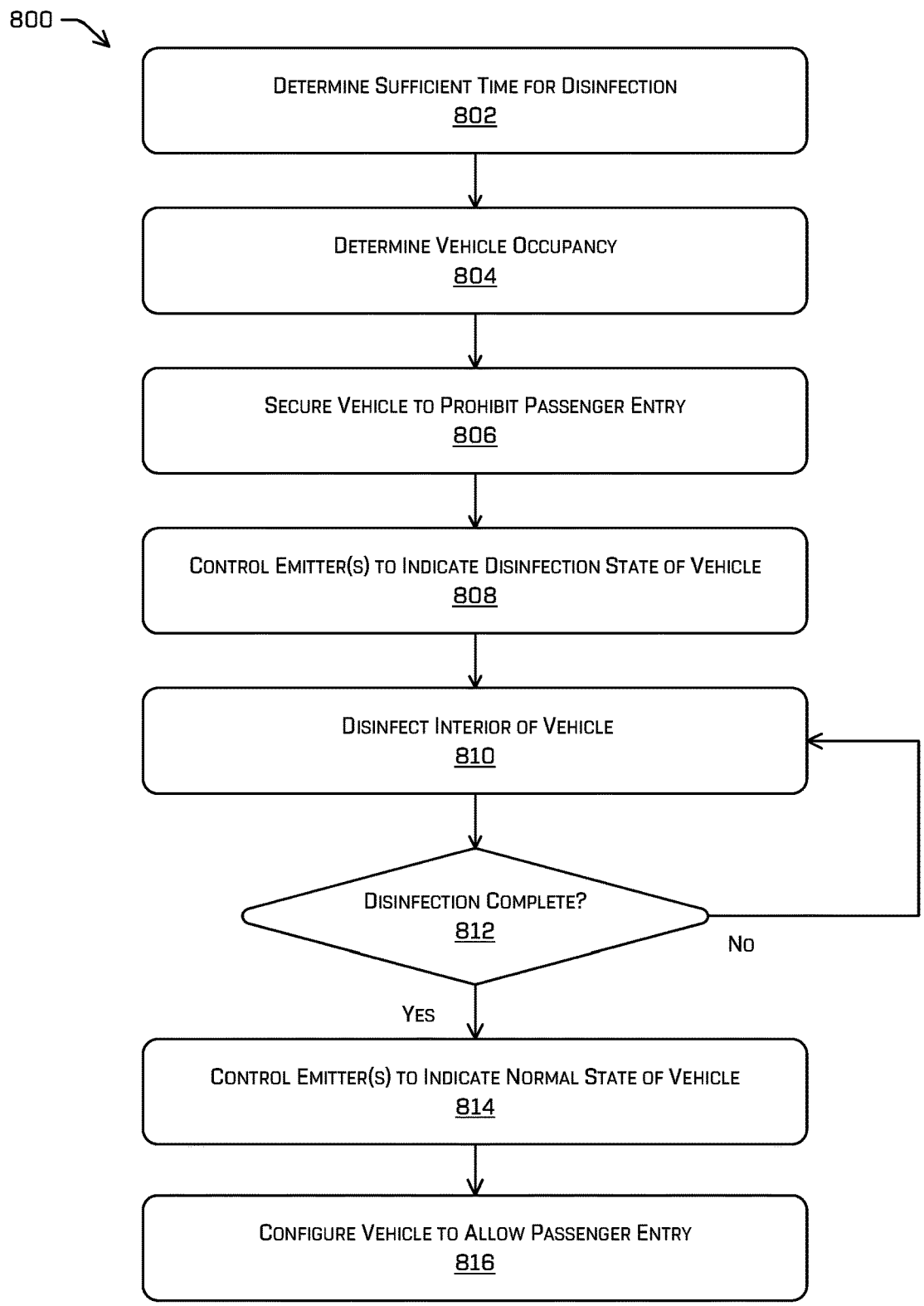
FIG. 8 is a flowchart illustrating an example method for disinfecting a vehicle, according to aspects of this disclosure.
Figure 9:
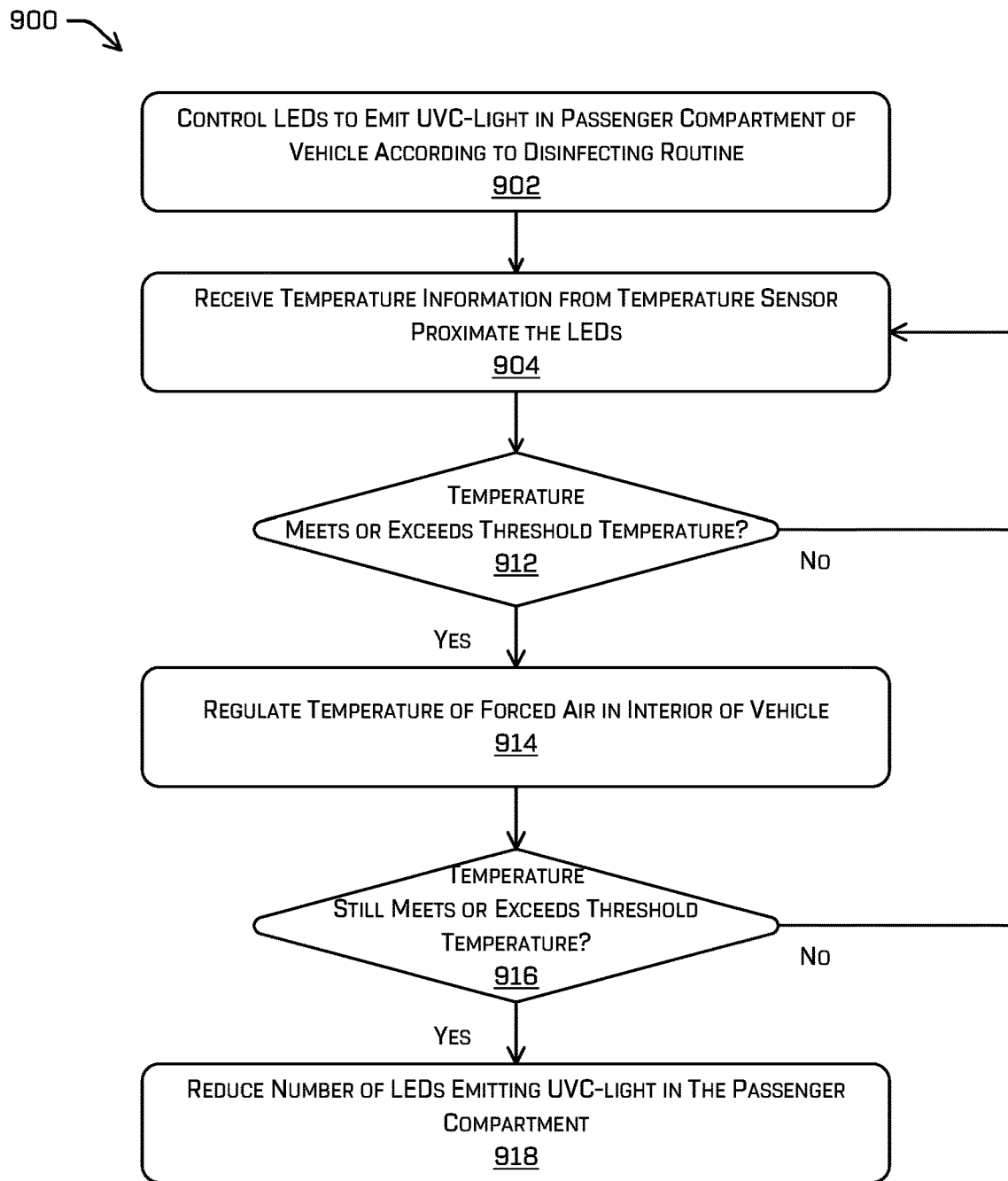
FIG. 9 is a flowchart illustrating another example method for disinfecting a vehicle, according to aspects of this disclosure.

FIGS. 8 and 9 illustrate example processes in accordance with embodiments of the disclosure. These processes are illustrated as logical flow graphs, each operation of which represents a sequence of operations that can be implemented in hardware, software, or a combination thereof. In the context of software, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described operations can be combined in any order and/or in parallel to implement the processes.

FIG. 8 depicts an example process 800 for disinfecting an interior of a vehicle, such as an autonomous vehicle. In examples, some or all of the process 800 can be performed by the vehicle system(s) 132 and/or by one or more components illustrated in FIG. 7, as described herein. For example, some or all of the process 800 can be performed by the sensor system(s) 706, the planning component 728, the system controller(s) 730, the disinfecting system 732, the climate control system 716, and/or the safety system(s) 718. However, the process 800 is not limited to being performed by these systems and components, and those systems and components are not limited to performing the process 800.

At an operation 802, the process 800 includes determining a sufficient time for disinfection. In examples, the process 800 is applied to autonomous vehicles, such as one of the autonomous vehicles 600, 702 described above. The autonomous vehicles 600, 702 may be configured to transport passengers and/or cargo between locations. Because a number of passengers and/or things may be transported in the autonomous vehicle 702, it may be necessary to periodically disinfect the passenger/cargo compartment. Examples of this disclosure relates to using LEDs that emit UVC light for a predetermined period of time sufficient to disinfect surfaces when the passenger compartment. In some examples, the amount of time necessary to completely disinfect the passenger compartment (or to an acceptable degree) may vary based on a number of UVC light-emitting sources disposed in the passenger compartment, positions of those sources, a distance of those sources from a surface to be disinfected, or the like.

At the operation 802, a disinfecting time, e.g., a time necessary to disinfect the passenger/cargo compartment to a desired degree may be compared to a time at which a next passenger is to be retrieved. For instance, the operation 802 can include receiving information about a next destination of the autonomous vehicle and/or a transit time to that destination. As described in some examples herein, the next destination for the autonomous vehicle may be selected to ensure that the transit time to the next destination is equal to or greater than a disinfecting time.

In some examples, a disinfecting time may be based on a time or activity within the vehicle. For example, if a disinfection routine is not activated for a relatively long period of time, a cabin of a vehicle may be determined to require a higher degree of disinfection. Similarly, if it is raining or humid, the cabin may be determined to require a higher degree of disinfection as the cabin may present a more inviting environment for pathogens under these conditions. In some examples, operation of an autonomous vehicle between driving locations may now provide sufficient and regulated time for disinfecting the vehicle and thus it may be determined that a higher degree of disinfection is necessary when a disinfecting routine is activated. Thus, environmental, occupancy, usage, historic time, or other data may be used to determine or modify a disinfecting time at operation 802.

At an operation 804, the process 800 can include determining a vehicle occupancy. For example, it may be desirable to avoid exposing passengers and/or certain cargo to UVC light emitted according to implementations of this disclosure. Accordingly, the operation 804 may include determining that the vehicle is free of passengers and/or cargo that may be adversely affected by UVC-light. Without limitation, the operation 804 can include receiving information from one or more of the sensor system(s) 706 and determining, from the sensor information, that the autonomous vehicle 702 is empty. In some examples, a mobile device (e.g., a smartphone) or similar device can be used to determine occupancy of a vehicle and/or future occupancy of a vehicle especially as such devices are used by users of an autonomous vehicle to arrange and/or plan use of the autonomous vehicle for transportation.

At an operation 806, the process 800 can include securing the vehicle to prohibit passenger entry. As detailed above, an interior of the vehicle may be disinfected when the vehicle is free of passengers. Thus, while the operation 804 may be executed to determine the no passengers are in the vehicle, the operation 806 may be executed to ensure that passengers do not enter the vehicle during a disinfecting cycle. In some examples, the operation 806 can include controlling one or more of the safety system(s) 718. Without limitation, the safety system(s) 718 can include locks or other actuators that secure doors or other coverings in a closed position.

At an operation 808, the process 800 can also include controlling emitters to indicate a disinfection state of the vehicle. For example, in addition to securing the vehicle to prevent passenger ingress, a state of the vehicle may also be changed to indicate to would-be-passengers that the vehicle is currently undergoing disinfection. In some examples, visible light emitters may be changed to a predetermined color or light pattern that indicates the status. In other examples, a display or other user interface of the vehicle may be changed to indicate the state. Audio emitters may also be used e.g., to convey audibly that the vehicle is undergoing a disinfecting procedure.

At an operation 810, the process 800 can include disinfecting the interior of the vehicle. For example, and as described herein, aspects of this disclosure include incorporating a plurality of LEDs that emit UVC light into a light assembly in the vehicle. In examples, the light assembly can be coupled to a ceiling of the autonomous vehicle such that the UVC light-emitting LEDs are configured to emit the UVC light on surfaces within the passenger compartment that are typically contacted by a passenger. Some such surfaces can include seats, seatbelts, and/or other user interface elements. As described herein, a disinfecting routine can include emitting UVC light for a predetermined amount of time and/or using a predetermined number of emitters. In some examples, the vehicle 702, e.g. at the disinfecting system 732, can include a number of disinfecting routines, one of which may be selected and executed at the operation 810.

At an operation 812, it is determined whether disinfection is complete. For instance, if at the operation 812, is determined that the disinfection routine is not complete, the operation 810 may continue. As described herein, a disinfection routine may be associated with a predetermined time, and the operation 812 make include determining whether that time has elapsed.

Alternatively, if at the operation 812 it is determined that disinfection is complete, the process 800 proceeds to an operation 814 that includes controlling emitters to indicate a normal state of the vehicle. For example, the operation 814 may be similar to the operation 808, but instead of indicating that the vehicle is not ready for passengers, e.g. because of an in-process disinfecting routine, at the operation 814, the vehicle is configured to indicate to would-be passengers that they may enter the vehicle. For instance, visible light emitters associated with the vehicle may be configured to emit light at a different wavelength and/or according to a different emission pattern, e.g., different from the wavelength and/or pattern associated with the operation 808, to indicates that the vehicle is ready for transporting passengers. The operation 814 may also include configuring a display associated with the vehicle to indicate that the vehicle is ready to transport a passenger. Moreover, the operation 814 can include generating an audible output such as an instruction to enter the vehicle.

At the operation 816, the process 800 can configure the vehicle to allow passenger entry. In some examples, the operation 816 can include unlocking a door or other ingress covering and/or opening a door to allow ingress into the vehicle.

The process 800 provides for disinfecting of an autonomous vehicle without the need to remove the vehicle from service, e.g., because the disinfecting can be done in between a first time at which the vehicle delivers a passenger or cargo to a destination and a second time at which the vehicle arrives at a new location to retrieve a new passenger or cargo. Moreover, by leveraging systems within the autonomous vehicle, such as sensor systems and/or safety systems, the process 800 can ensure that disinfection is done safely, e.g., without adverse effects to passengers and/or cargo. As will also be appreciated, the process 800 kills and/or eliminates harmful bacteria and viruses, without the need for chemicals and/or human interaction.

Aspects of the process 800 may be particularly well suited for performance by the LEDs of the lighting assemblies 126, 300, however, the process 800, including the operation 810, is not limited to being performed by LEDs in a lighting assembly like the lighting assemblies 126, 300. Without limitation, any arrangement or type of UVC light emitters may be used to implement a disinfecting routine using the techniques described herein.

FIG. 9 illustrates a process 900 for disinfecting an enclosed volume, such as an interior of a vehicle. For example, the process 900 may be implemented to disinfect an interior of an autonomous vehicle using UVC-light. In examples, some or all of the process 900 can be performed by the light assembly 126, the vehicle system(s) 132, the light assembly 300, and/or by one or more components illustrated in FIG. 7, as described herein. For example, some or all of the process 900 can be performed by the sensor system(s) 706, the system controller(s) 730, the disinfecting system 732, the climate control system 716, and/or the safety system(s) 718. However, the process 900 is not limited to being performed by these systems and components, and those systems and components are not limited to performing the process 900.

At an operation 902, the process 900 includes controlling LEDs to emit UVC light in a passenger compartment of a vehicle according to a disinfecting routine. In examples described in this disclosure, LEDs may be disposed in a housing of a lighting assembly, such as the lighting assembly 126 shown in FIG. 1 and/or the lighting assembly 300 shown in FIGS. 3-5. In some examples, a first plurality of LEDs may be configured above, or otherwise in association with a first seating area, and a second plurality of LEDs may be configured above, or otherwise in association with a second seating area. The LEDs may be controllable to emit UVC light in the passenger compartment of the vehicle generally as described herein. As also described, the disinfecting system 732 or other components may be configured to control the UVC light-emitting LEDs according to a predetermined routine, e.g., for a predetermined time.

At an operation 904, the process 900 includes receiving temperature information from a temperature sensor proximate the LEDs. In some examples, LEDs that emit UVC light may generate thermal energy. In some instances, particularly when multiple UVC light-emitting LEDs are used, thermal energy can be destructive to components in the vehicle, including substrates on which the LEDs are disposed, housings containing the LEDs, or the like. A temperature sensor, which may be embodied as the temperature sensor 428 and/or one of the sensor system(s) 706, may be disposed proximate the LEDs, e.g., on a substrate carrying the LEDs, to monitor temperature. In at least some examples, the temperature sensor may be embodied as a thermistor on a PCBA. In some examples, heat associated with operation of LEDs can be characterized to avoid use of a temperature sensor. For example, an operational state, operational time, applied voltage, applied current, or other attribute can be used to estimate a temperature of an LED.

At an operation 912, the process 900 includes determining whether a sensed temperature meets or exceeds a threshold temperature. For instance, the sensed temperature may be determined from the temperature information received at the operation 904. In examples, the operation 912 may include comparing the received temperature information to one or more predetermined temperature thresholds. For example, the temperature thresholds may be maximum temperatures above which damage to the LEDs, the substrate carrying the LEDs, and/or other components may occur. Alternatively, the temperature thresholds may be temperatures below such maximum temperatures.

If, at the operation 912 it is determined that the temperature determined from the temperature information received at the operation 904 does not meet or exceed the threshold temperature, the process 900 returns to the operation 904. In some examples, the temperature information may be received at a frequency, e.g., once a second, once a millisecond, or the like, e.g., depending on the functionality and capabilities of the temperature sensor and/or other systems.

Alternatively, if at the operation 912 it is determined that the temperature determined using the received temperature information does meet or exceed the threshold temperature, the process 900 includes, at an operation 914, regulating a temperature of forced air in the interior of the vehicle. In examples described herein, one or more heatsinks may be associated with the LEDs that emit the UVC-light, and the heatsinks may be disposed in airflow generated by a climate control system of the vehicle. For example, FIG. 4 shows a heatsink 404 disposed in a flow of temperature-regulated air forced into a passenger compartment associated with a vehicle via the duct 410. Accordingly, when the temperature is found to be above a threshold temperature, the operation 914 may force air over the heatsinks and/or cause air forced over the heatsinks to be reduced in temperature. For instance, aspects of this disclosure include controlling the climate control system generally used for passenger comfort to enhance heat dissipation caused by use of UVC light-emitting LEDs.

At an operation 916, the process 900 includes determining whether the temperature meets or exceeds the threshold temperature. For instance, the operation 916 may be the same as the operation 912, and accordingly, may be based on temperature information received at the operation 904. The operation 916 may determine whether temperature regulation undertaken at the operation 914 was successful in reducing the temperature proximate the LEDs. In some instances, the threshold temperature associated with the operation 916 may be the same as the threshold associated with the operation 912.

If, at the operation 916 it is determined that the temperature does not meet or exceed the threshold temperature, the process 900 may return to the operation 904 e.g., to continue to monitor the temperature proximate the LEDs.

Alternatively, if at the operation 916 it is determined that the temperature does meet or exceed the threshold temperature, the process 900 may, at an operation 918, reduce a number of LEDs emitting UVC light into the passenger compartment or reduce power provided to the LEDs such that they operate in a lower power state (and optionally increasing a time for a disinfection cycle). Stated differently, if regulating the temperature of the forced air in the interior of the vehicle was insufficient to reduce the temperature proximate the LEDs below a threshold temperature, the process 900 can discontinue the disinfecting routine entirely. Alternatively, the operation 918 can include reducing a number of the LEDs that are emitting UVC light e.g., to decrease the thermal load associated with the cleaning system described herein. While reducing the number of LEDs emitting the UVC light may reduce efficacy of disinfection, the reduced number will still continue to provide some level of disinfection. Moreover, and although not illustrated in the process 900, the temperature may continue to be regulated e.g., as at the operations 104, 906, and LEDs deactivated at the operation 918 may be reactivated, e.g. until such time as the disinfecting routine is complete.

According to aspects of this disclosure, disinfecting routines may be implemented using LEDs that emit UVC-light. Moreover, because UVC light-emitting LEDs may create relatively large thermal loads, this disclosure provides techniques and systems for monitoring a temperature and/or reducing the temperature using active cooling techniques.

Throughout this disclosure, references to "instances" may indicate that various instance(s) of the present disclosure may include a particular feature, structure, or characteristic, but not every instance necessarily includes the particular feature, structure, or characteristic. Further, repeated use of the phrase "in some instances" does not necessarily refer to the same instance, although it may.

In the description and claims, the terms "coupled" and "connected," along with their derivatives, may be used. It should be understood that these terms may be not intended as synonyms for each other. Rather, in particular embodiments, "connected" may be used to indicate that two or more elements are in direct physical or electrical contact with each other. "Coupled" may mean that two or more elements are in direct physical or electrical contact. However, "connected" and "coupled" may also mean that two or more elements are not in direct contact with each other, but yet still co-operate or interact with each other.

Although the discussion above sets forth example implementations of the described techniques, other architectures may be used to implement the described functionality, and are intended to be within the scope of this disclosure. Furthermore, although specific distributions of responsibilities are defined above for purposes of discussion, the various functions and responsibilities might be distributed and divided in different ways, depending on circumstances.

Furthermore, although the subject matter has been described in language specific to structural features and/or methodological acts, it is to be understood that the subject matter defined in the appended claims is not necessarily limited to the specific features or acts described. Rather, the specific features and components are disclosed as exemplary forms of implementing the claims.

EXAMPLE CLAUSES

A: An example vehicle includes: a passenger compartment including a ceiling; a climate control system configured to cause forced air into the passenger compartment via an opening in the ceiling; and a light assembly coupled to the ceiling, the light assembly comprising: a light-emitting diode (LED) configured to emit UVC light into the passenger compartment, and a heat sink thermally coupled to the LED and disposed in a path of the forced air such that the forced air impinges on the heat sink entering the passenger compartment.

B: The vehicle of example A, further comprising: a passenger seat disposed in the passenger compartment, wherein the LED is configured to emit the UVC light onto the passenger seat.

C: The vehicle of example A or example B, wherein: the passenger seat comprises a first passenger seat; the LED is one of a first plurality of LEDs at a first position above the first passenger seat to emit the UVC light onto the first passenger seat; the vehicle further comprises a second passenger seat disposed in the passenger compartment; and the light assembly further comprises a second plurality of LEDs configured to emit UVC light onto the second passenger seat.

D: The vehicle of any one of example A through example C, wherein the climate control system is configured to regulate a temperature of the forced air.

E: The vehicle of any one of example A through example D, further comprising a temperature sensor thermally coupled to the LED, the climate control system being controlled based at least in part on a signal generated by the temperature indicative of a temperature of the LED.

F: A system for disinfecting an enclosed volume, the system comprising: a climate control system configured to force air into a space; and a light assembly comprising: a light emitter configured to emit light onto one or more surfaces in the space, and a heat sink thermally coupled to the light emitter and disposed in a path of the air forced into the space.

G: The system of example F, wherein the light assembly further comprises: a housing, the housing including one or more openings optically aligned with the light emitter and through which the light passes.

H: The system of example F or example G, wherein the housing defines an ingress via which the air enters the housing and an egress via which the air exits the housing into the space, the housing further defining a passageway between the ingress and the egress, wherein the heat sink is at least partially disposed in the passageway.

I: The system of any one of example F through example H, wherein the light assembly further comprises one or more visible light sources and the housing includes one or more additional openings through which visible light emitted by the visible light sources passes, the visible light sources being configured to illuminate at least one of a seat or a floor in the space.

J: The system of any one of example F through example I, wherein: the one or more visible light sources are configured to emit visible light of at least two wavelengths, and the light assembly is configurable in a first configuration or a second configuration, in the first configuration the light emitter emits UVC light and the one or more visible light sources emit visible light at a first wavelength and in the second configuration the light emitter does not emit the UVC light and the one or more visible light sources emit the visible light at a second wavelength.

K: The system of any one of example F through example J, wherein the climate control system is configured to regulate a temperature of the air forced into the space.

L: The system of any one of example F through example K, further comprising: a temperature sensor disposed to generate an output based at least in part on a temperature corresponding to the light emitter, the climate control system being controlled, at least in part, on an output of the temperature sensor.

M: The system of any one of example F through example L, wherein: the system comprises a vehicle, the space comprises a passenger compartment including one or more passenger seats; and the light emitter is configured to emit UVC light at least partially onto the one or more passenger seats.

N: The system of any one of example F through example M, further comprising: a door movable between a first position allowing passenger access to the space from outside the vehicle and a second position preventing access to the space from outside the vehicle; and a lock configured to selectively secure the door in the second position, the light emitter being controlled based at least in part on the door being secured in the second position.

O: An example vehicle includes: a passenger compartment; a passenger seat disposed in the passenger compartment; a climate control system configured to force air into the passenger compartment; and a light assembly comprising: a visible light source configured to emit visible light; a UVC light emitter configured to emit UVC light, and a heat sink thermally coupled to the UVC light emitter and disposed in a path of the temperature-regulated air forced into the passenger compartment.

P: The vehicle of example O, wherein the passenger compartment comprises a ceiling, the light assembly is coupled to the ceiling, the light assembly further comprising: a housing containing the heat sink and including one or more openings optically aligned with the UVC light emitter and through which the UVC light passes.

Q: The vehicle of example O or example P, the housing further defining an ingress via which the air enters the housing and an egress via which the temperature-regulated air exits the housing into the passenger compartment, the housing further defining a passageway between the ingress and the egress, wherein the heat sink is at least partially disposed in the passageway.

R: The vehicle of any one of example O through example Q, wherein the light assembly further comprises a user-interactive selection button selectable by a user to transmit a signal to a computing system of the vehicle.

S: The vehicle of any one of example O through example R, further comprising: a temperature sensor disposed to generate an output based at least in part on a temperature proximate the UVC light emitter, the temperature control system being controlled, at least in part, on an output of the temperature sensor.

T: The vehicle of any one of example O through example S, wherein: the passenger seat comprises a first seating area and at least one first passenger accessory associated with the first seating area and a second seating area and at least one second passenger accessory associated with the second seating area, and the UVC light emitter comprises a first emitter disposed above the first seating area and configured to emit light onto the first seating area and the at least one first passenger accessory and a second emitter disposed above the second seating area and configured to emit light onto the second seating area and the at least one second passenger accessory.

CONCLUSION

While one or more examples of the techniques described herein have been described, various alterations, additions, permutations and equivalents thereof are included within the scope of the techniques described herein.

In the description of examples, reference is made to the accompanying drawings that form a part hereof, which show by way of illustration specific examples of the claimed subject matter. It is to be understood that other examples can be used and that changes or alterations, such as structural changes, can be made. Such examples, changes or alterations are not necessarily departures from the scope with respect to the intended claimed subject matter. While the steps herein can be presented in a certain order, in some cases the ordering can be changed so that certain inputs are provided at different times or in a different order without changing the function of the systems and methods described. The disclosed procedures could also be executed in different orders. Additionally, various computations described herein need not be performed in the order disclosed, and other examples using alternative orderings of the computations could be readily implemented. In addition to being reordered, in some instances, the computations could also be decomposed into sub-computations with the same results.

What is claimed is:

1. A vehicle comprising:
a passenger compartment including a ceiling;
a climate control system configured to force air into the passenger compartment via a conduit; and
a light assembly coupled to the ceiling, the light assembly comprising:
a housing coupled to and in fluid communication with the conduit, the housing defining an ingress via which forced air from the climate control system enters the housing and an egress via which the forced air exits the housing into the passenger compartment;
a light-emitting diode (LED) configured to emit UVC light into the passenger compartment; and
a heat sink thermally coupled to the LED and disposed in a path of the forced air such that the forced air impinges on the heat sink entering the passenger compartment.

2. The vehicle of claim 1, further comprising:
a passenger seat disposed in the passenger compartment, wherein the LED is configured to emit the UVC light onto the passenger seat.

3. The vehicle of claim 2, wherein:
the passenger seat comprises a first passenger seat;
the LED is one of a first plurality of LEDs at a first position above the first passenger seat to emit the UVC light onto the first passenger seat;
the vehicle further comprises a second passenger seat disposed in the passenger compartment; and
the light assembly further comprises a second plurality of LEDs configured to emit UVC light onto the second passenger seat.

4. The vehicle of claim 1, wherein the climate control system is configured to regulate a temperature of the forced air.

5. The vehicle of claim 4, further comprising a temperature sensor thermally coupled to the LED, the climate control system being controlled based at least in part on a signal generated by the temperature indicative of a temperature of the LED.

6. The vehicle of claim 1, further comprising:
a disinfecting system comprising the light-emitting diode (LED) configured to emit UVC light into the passenger compartment, the disinfecting system configured to receive a transit time from a planning component of the vehicle and operate based at least in part on the transit time.

7. A system for disinfecting an enclosed volume in a vehicle, the system comprising:
a climate control system configured to force air into a space via a conduit; and
a light assembly comprising:
a housing coupled to and in fluid communication with the conduit, the housing defining an ingress via which forced air from the climate control system enters the housing and an egress via which the forced air exits the housing;
a light emitter configured to emit light onto one or more surfaces in the space; and
a heat sink thermally coupled to the light emitter and disposed in a path of the air forced into the space.

8. The system of claim 7, wherein
the housing includes one or more openings optically aligned with the light emitter and through which the light passes.

9. The system of claim 8, wherein the housing further defines a passageway between the ingress and the egress, wherein the heat sink is at least partially disposed in the passageway.

10. The system of claim 8, wherein the light assembly further comprises one or more visible light sources and the housing includes one or more additional openings through which visible light emitted by the one or more visible light sources passes, the one or more visible light sources being configured to illuminate at least one of a seat or a floor in the space.

11. The system of claim 10, wherein:
the one or more visible light sources are configured to emit visible light of at least two wavelengths, and
the light assembly is configurable in a first configuration or a second configuration, in the first configuration the light emitter emits UVC light and the one or more visible light sources emit visible light at a first wavelength and in the second configuration the light emitter does not emit the UVC light and the one or more visible light sources emit the visible light at a second wavelength.

12. The system of claim 7, wherein the climate control system is configured to regulate a temperature of the air forced into the space.

13. The system of claim 12, further comprising:
a temperature sensor disposed to generate an output based at least in part on a temperature corresponding to the light emitter, the climate control system being controlled, at least in part, on an output of the temperature sensor.

14. The system of claim 7, wherein:
the system comprises a vehicle,
the space comprises a passenger compartment including one or more passenger seats; and
the light emitter is configured to emit UVC light at least partially onto the one or more passenger seats.

15. The system of claim 14, further comprising:
a door movable between a first position allowing passenger access to the space from outside the vehicle and a second position preventing access to the space from outside the vehicle; and
a lock configured to selectively secure the door in the second position, the light emitter being controlled based at least in part on the door being secured in the second position.

16. A vehicle comprising:
a passenger compartment;
a passenger seat disposed in the passenger compartment;
a climate control system configured to force air into the passenger compartment via a conduit; and
a light assembly comprising:
a housing coupled to and in fluid communication with the conduit, the housing defining an ingress via which forced air from the climate control system enters the housing and an egress via which the forced air exits the housing into the passenger compartment;
a visible light source configured to emit visible light;
a UVC light emitter configured to emit UVC light; and
a heat sink thermally coupled to the UVC light emitter and disposed in a path of the air forced into the passenger compartment.

17. The vehicle of claim 16, wherein the passenger compartment comprises a ceiling, the light assembly is coupled to the ceiling, and wherein the housing contains the heat sink and includes one or more openings optically aligned with the UVC light emitter and through which the UVC light passes.

18. The vehicle of claim 16, wherein the light assembly further comprises a user-interactive selection button selectable by a user to transmit a signal to a computing system of the vehicle.

19. The vehicle of claim 16, further comprising:
a temperature sensor disposed to generate an output based at least in part on a temperature proximate the UVC light emitter, the climate control system being controlled, at least in part, on an output of the temperature sensor.

20. The vehicle of claim 16, wherein:
the passenger seat comprises a first seating area and at least one first passenger accessory associated with the first seating area and a second seating area and at least one second passenger accessory associated with the second seating area, and
the UVC light emitter comprises a first emitter disposed above the first seating area and configured to emit light onto the first seating area and the at least one first passenger accessory and a second emitter disposed above the second seating area and configured to emit light onto the second seating area and the at least one second passenger accessory.

* * * * *